(12) United States Patent
Ohtani et al.

(10) Patent No.: US 12,312,294 B2
(45) Date of Patent: May 27, 2025

(54) ANTHRAQUINONE COMPOUND, LIQUID CRYSTAL COMPOSITION CONTAINING SAID COMPOUND, AND DIMMING ELEMENT

(71) Applicant: NIPPON KAYAKU KABUSHIKI KAISHA, Tokyo (JP)

(72) Inventors: Kohei Ohtani, Tokyo (JP); Hitomi Muto, Tokyo (JP); Yu Hattori, Tokyo (JP); Saori Suzuki, Tokyo (JP)

(73) Assignee: NIPPON KAYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 18/698,038

(22) PCT Filed: Oct. 14, 2022

(86) PCT No.: PCT/JP2022/038309
§ 371 (c)(1),
(2) Date: Apr. 3, 2024

(87) PCT Pub. No.: WO2023/063408
PCT Pub. Date: Apr. 20, 2023

(65) Prior Publication Data
US 2024/0409497 A1  Dec. 12, 2024

(30) Foreign Application Priority Data
Oct. 14, 2021 (JP) ................. 2021-169127

(51) Int. Cl.
*G02F 1/1333* (2006.01)
*C07C 229/74* (2006.01)
(Continued)

(52) U.S. Cl.
CPC .......... *C07C 229/74* (2013.01); *C09K 19/322* (2013.01); *C09K 19/52* (2013.01); *G02F 1/13* (2013.01)

(58) Field of Classification Search
CPC ...... C09K 19/12; C09K 19/322; C09K 19/60; C09K 19/603; C09K 2019/0448; G03F 1/1333; G03F 1/1334
See application file for complete search history.

(56) References Cited

U.S. PATENT DOCUMENTS 4,301,080 A * 11/1981 Adam .................. C09B 1/525
552/250
4,505,549 A    3/1985 Shimidzu et al.
(Continued)

FOREIGN PATENT DOCUMENTS

CN    108663866 A    10/2018
JP    57-90053 A    6/1982
(Continued)

OTHER PUBLICATIONS

International Search Report Mailed Dec. 27, 2022 in corresponding PCT application No. PCT/JP2022/038309.

*Primary Examiner* — Geraldina Visconti
(74) *Attorney, Agent, or Firm* — Nields, Lemack & Frame, LLC

(57) ABSTRACT

An anthraquinone compound represented by formula (1): (where $R_1$ and $R_4$ represent —H, a C1-C12 alkyl group, a C1-C12 alkyl group, a halogen atom, —$CO_2R_9$, —$OCOR_9$, —$COR_9$, a cyano group, or —$CF_3$, $R_2$, $R_3$, $R_5$ and $R_6$ represent —H, a C1-C4 alkyl group, a C1-C4 alkoxy group, a halogen atom, —$CO_2R_9$, —$OCOR_9$, —$COR_9$, a cyano group, or —$CF_3$. $R_7$ and $R_8$ represent —H, a C1-C12 alkyl group, or a C1-C12 alkoxy group. $R_9$ represents a C1-C12 alkyl group, or a substituent represented by formula (a) (where $R_{10}$ represents —H, a C1-C8 alkyl group, or a C1-C8 alkoxy group) or formula (b) (where $R_{11}$ represents —H or a C1-C8 alkyl group); however, at least one of $R_1$ through $R_6$ represents a halogen atom, —$CO_2R_9$, —$COR_9$, a cyano group, or —$CF_3$).

(1)

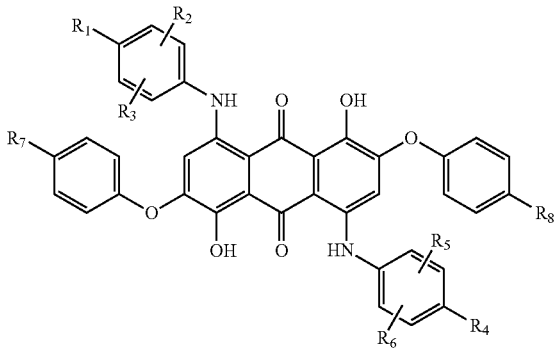

(a)

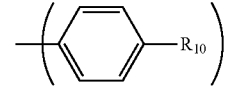

(b)

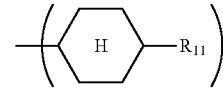

15 Claims, No Drawings

(51) Int. Cl.
*C09K 19/32* (2006.01)
*C09K 19/52* (2006.01)
*G02F 1/13* (2006.01)

(56) References Cited

U.S. PATENT DOCUMENTS

| | | | |
|---|---|---|---|
| 12,157,851 B2 * | 12/2024 | Ohtani | ............ C09B 1/51 |
| 2015/0218455 A1 | 8/2015 | Xu et al. | |
| 2024/0141234 A1 * | 5/2024 | Muto | ............ C08F 2/50 |
| 2024/0400899 A1 * | 12/2024 | Muto | ............ C09K 19/12 |
| 2024/0409497 A1 * | 12/2024 | Ohtani | ............ C07C 225/36 |

FOREIGN PATENT DOCUMENTS

| | | | |
|---|---|---|---|
| JP | 57-126879 A | 8/1982 | |
| JP | 58-63778 A | 4/1983 | |
| JP | 62-5941 A | 1/1987 | |
| JP | 63-501512 A | 6/1988 | |
| JP | 3-47392 A | 2/1991 | |
| JP | 5-2194 A | 1/1993 | |
| JP | 5-173114 A | 7/1993 | |
| JP | 2007-199333 A | 8/2007 | |
| JP | 2011-190314 A | 9/2011 | |
| JP | 2018-205746 A | 12/2018 | |
| JP | 2020-84149 A | 6/2020 | |

* cited by examiner

ANTHRAQUINONE COMPOUND, LIQUID CRYSTAL COMPOSITION CONTAINING SAID COMPOUND, AND DIMMING ELEMENT

TECHNICAL FIELD

The present invention relates to a novel anthraquinone compound, a liquid crystal composition containing the compound, and a light control element.

BACKGROUND ART

In vehicles such as trains and automobiles, and windows, doors, partitions, and the like of buildings such as business buildings and hospitals, various devices related to light control films for controlling transmission of external light have been proposed for the purpose of protecting privacy and the like (see Patent Literatures 1 and 2). Examples of such light control films include ones utilizing a liquid crystal. Usually, the liquid crystal light control film can block a field of view by controlling transmission and scattering of light depending on whether or not a voltage is applied, but cannot block light itself, and therefore glare tends to increase due to light scattering. Therefore, for the purposes of reducing glare, improving contrast, and the like, attempts have been made to use a dye as a material of a light control panel (see Patent Literatures 3 and 4). For example, in the case of using such a light control panel for a window glass of an automobile, from the viewpoints of practicality and designability, there is a strong demand for a light control element having a small change in color tone not only at the time of light shielding but also at the time of transparency when exposed to light for a long period of time in outdoor use, that is, at high temperatures for a long period of time, in addition to having good visibility without fogging at the time of transparency.

Dichroic dyes have been commonly known as the dyes to be used in liquid crystal light control films. As a light control element using a liquid crystal composition containing a dichroic dye, GH (guest-host) type has been known, and various dichroic dyes have been proposed (see Patent Literature 5).

Such dichroic dyes are required to have not only contrast when used as a display element, but also light resistance, UV resistance, heat resistance, and the like. Attempts have been made to improve these properties, but those satisfying such properties have not been found. For example, Patent Literature 5 discloses a dichroic dye suitable for light control applications, but the dye of Patent Literature 5 has insufficient light resistance.

CITATION LIST

Patent Literatures

PATENT LITERATURE 1: JPS63-501512A
PATENT LITERATURE 2: JPH03-47392A
PATENT LITERATURE 3: JP2018-205746A
PATENT LITERATURE 4: JP2011-190314A
PATENT LITERATURE 5: JPS62-5941A

SUMMARY OF INVENTION

Technical Problem

A first object of the present invention is to provide a novel anthraquinone compound.

Another object of the present invention is to provide a dichroic dye which is the novel anthraquinone compound and is excellent in light resistance, a liquid crystal composition containing the dichroic dye, and a light control element containing the composition.

Solution to Problem

The present inventors have succeeded in obtaining a novel anthraquinone compound having a specific structure.

The present inventors have also found that a light control element having excellent light resistance can be obtained by using a liquid crystal composition containing a dichroic dye which is such a novel anthraquinone compound having a specific structure.

That is, aspects or embodiments included in the present invention are as follows.

[1]. An anthraquinone compound represented by the following formula (1):

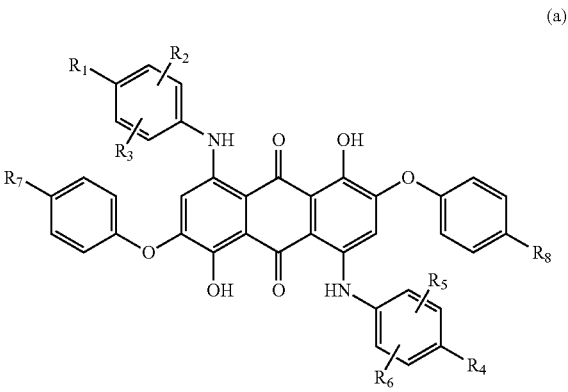

(a)

wherein $R_1$ and $R_4$ each independently represent a hydrogen atom, a C1-C12 linear or branched alkyl group, a C1-C12 linear or branched alkoxy group, a halogen atom, $-CO_2R_9$, $-OCOR_9$, $-COR_9$, a cyano group, or a trifluoromethyl group, $R_2$, $R_3$, $R_5$, and $R_6$ each independently represent a hydrogen atom, a C1-C4 linear or branched alkyl group, a C1-C4 linear or branched alkoxy group, a halogen atom, $-CO_2R_9$, $-OCOR_9$, $-COR_9$, a cyano group, or a trifluoromethyl group, $R_7$ and $R_8$ each independently represent a hydrogen atom, a C1-C12 linear or branched alkyl group, or a C1-C12 linear or branched alkoxy group, and $R_9$ each independently represents a C1-C12 linear or branched alkyl group or a substituent represented by the following formula (a):

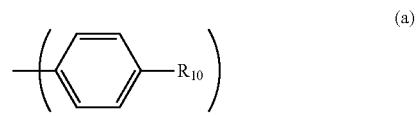

(a)

(wherein $R_{10}$ represents a hydrogen atom, a C1-C8 linear or branched alkyl group or a C1-C8 linear or branched alkoxy group) or represented by the following formula (b):

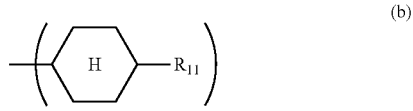

(wherein $R_{11}$ represents a hydrogen atom or a C1-C8 linear or branched alkyl group), provided that at least one of $R_1$ to $R_6$ represents a halogen atom, $-CO_2R_9$, $-COR_9$, a cyano group, or a trifluoromethyl group.

[2]. The anthraquinone compound according to [1], wherein $R_9$ is each independently a C1-C8 linear or branched alkyl group.

[3]. The anthraquinone compound according to [1] or [2], wherein in formula (1), $R_1$ and $R_4$ are each independently a hydrogen atom, a C1-C12 linear or branched alkyl group, a C1-C12 linear or branched alkoxy group, a fluorine atom, a chlorine atom, $-CO_2R_9$, $-COR_9$, a cyano group, or a trifluoromethyl group, and $R_2$, $R_3$, $R_5$, and $R_6$ are each independently a hydrogen atom, a C1-C4 linear or branched alkyl group, a C1-C4 linear or branched alkoxy group, a fluorine atom, a chlorine atom, $-CO_2R_9$, $-COR_9$, a cyano group, or a trifluoromethyl group.

[4]. The anthraquinone compound according to [3], wherein in formula (1). $R_1$ and $R_4$ are each independently a hydrogen atom, a C1-C12 linear or branched alkyl group, a fluorine atom, $-CO_2R_9$, $-COR_9$, a cyano group, or a trifluoromethyl group, and $R_2$, $R_3$, $R_5$, and $R_6$ are each independently a hydrogen atom, a C1-C4 linear or branched alkyl group, a fluorine atom, $-CO_2R_9$, $-COR_9$, a cyano group, or a trifluoromethyl group.

[5]. The anthraquinone compound according to any one of [1] to [4], wherein in formula (1), $R_2$ and $R_5$ are a hydrogen atom.

[6]. The anthraquinone compound according to any one of [1] to [5], wherein in formula (1), only one of $R_1$ and $R_3$ is a hydrogen atom, and only one of $R_4$ and $R_6$ is a hydrogen atom.

[7]. The anthraquinone compound according to any one of [1] to [6], wherein in formula (1), $R_3$ and $R_6$ are a hydrogen atom.

[8]. The anthraquinone compound according to any one of [1] to [7], wherein in formula (I), $R_4$ is a C4-C12 linear or branched alkyl group.

[9]. The anthraquinone compound according to any one of [1] to [8], wherein in formula (1), $R_7$ and $R_8$ are each independently a C4-C12 linear or branched alkyl group or a C4-C12 linear or branched alkoxy group.

[10]. A liquid crystal composition comprising the anthraquinone compound according to any one of [1] to [9] and a liquid crystal material.

[11]. The liquid crystal composition according to [10], further comprising at least one or more dye compounds other than the anthraquinone compound represented by formula (1).

[12]. The liquid crystal composition according to [10] or [11], further comprising a photocurable compound and a photopolymerization initiator.

[13]. A photocured product of the liquid crystal composition according to [12].

[14]. A light control element comprising the liquid crystal composition according to any one of [10] to [12] or the photocured product according to [13] sandwiched between a pair of substrates disposed opposite to each other, at least one of which is a transparent substrate having a transparent electrode.

[15]. The light control element according to [14], wherein both of the pair of substrates are transparent substrates having a transparent electrode.

Advantageous Effects of Invention

Since the anthraquinone compound of the present invention has dichroism and is excellent in light resistance, by using a liquid crystal composition containing the compound, a light control element having a small color change even when exposed to light at high temperatures for a long period of time not only at the time of light shielding but also at the time of transparency can be obtained.

DESCRIPTION OF EMBODIMENTS

Hereinafter, the present invention will be described in detail.

An anthraquinone compound of the present invention is represented by the following formula (1).

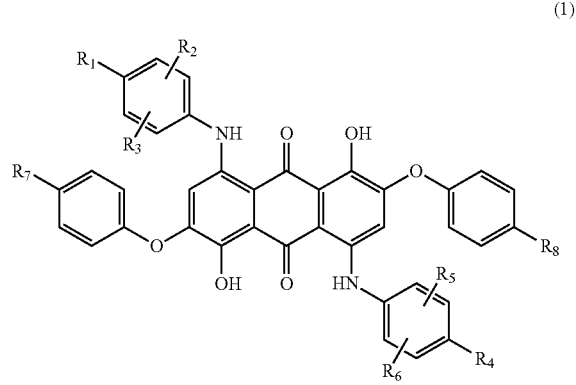

(1)

In formula (1), $R_1$ and $R_4$ each independently represent a hydrogen atom, a C1-C12 linear or branched alkyl group, a C1-C12 linear or branched alkoxy group, a halogen atom, $-CO_2R_9$, $-OCOR_9$, $-COR_9$, a cyano group, or a trifluoromethyl group. $R_2$, $R_3$, $R_5$, and $R_6$ each independently represent a hydrogen atom, a C1-C4 linear or branched alkyl group, a C1-C4 linear or branched alkoxy group, a halogen atom, $-CO_2R_9$, $-OCOR_9$, $-COR_9$, a cyano group, or a trifluoromethyl group. $R_7$ and $R_8$ each independently represent a hydrogen atom, a C1-C12 linear or branched alkyl group, or a C1-C12 linear or branched alkoxy group. $R_9$ each independently represents a C1-C12 linear or branched alkyl group or a substituent represented by the following formula (a) or (b). However, at least one of $R_1$ to $R_6$ represents a halogen atom, $-CO_2R_9$, $-COR_9$, a cyano group, or a trifluoromethyl group.

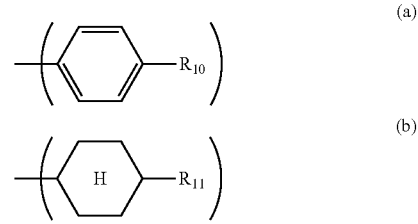

In formula (a), $R_{10}$ represents a hydrogen atom, a C1-C8 linear or branched alkyl group or a C1-C8 linear or branched alkoxy group, and in formula (b), $R_{11}$ represents a hydrogen atom or a C1-C8 linear or branched alkyl group.

The C1-C12 alkyl group represented by $R_1$ and $R_4$ in formula (1) may be linear or branched. thereof include a methyl group, an ethyl group, a n-propyl group, an iso-propyl group, a n-butyl group, an iso-butyl group, a sec-butyl group, a t-butyl group, a n-pentyl group, an iso-pentyl group, a neo-pentyl group, a t-pentyl group, a hexyl group, a heptyl group, an octyl group, a nonyl group, a decyl group, an undecyl group, a dodecyl group, a 2-ethylhexyl group, a 2-propylhexyl group, a 2-butylhexyl group, a 2-pentylhexyl group, and a 2-pentylheptyl group. Among them, a C4-C12 linear or branched alkyl group is preferable, a C4-C12 linear alkyl group is more preferable, and a C4-C8 linear alkyl group is still more preferable.

The C1-C12 alkoxy group represented by $R_1$ and $R_4$ in formula (1) may be linear or branched. Specific examples thereof include a methoxy group, an ethoxy group, a n-propoxy group, an iso-propoxy group, a n-butoxy group, an iso-butoxy group, a sec-butoxy group, a t-butoxy group, a n-pentyloxy group, an iso-pentyloxy group, a neo-pentyloxy group, a t-pentyloxy group, a hexyloxy group, a heptyloxy group, an octyloxy group, a nonyloxy group, a decyloxy group, an undecyloxyl group, a dodecyloxy group, a 2-ethylhexyloxy group, a 2-propylhexyloxy group, a 2-butylhexyloxy group, a 2-pentylhexyloxy group, and a 2-pentylheptyloxy group. Among them, a C1-C8 linear or branched alkoxy group is preferable, a C4-C8 linear or branched alkoxy group is more preferable, and a C4-C8 linear alkoxy group is still more preferable.

Specific examples of the halogen atom represented by $R_1$ and $R_4$ in formula (1) include a fluorine atom, a chlorine atom, a bromine atom, and an iodine atom. Among them, a fluorine atom or a chlorine atom is preferable, and a fluorine atom is more preferable.

Specific examples of the C1-C12 linear or branched alkyl group represented by $R_9$ include the same as the specific examples of the C1-C12 linear or branched alkyl group represented by $R_1$ and $R_4$ in formula (1), and are each independently preferably a C1-C8 linear or branched alkyl group, each independently more preferably a C1-C4 linear or branched alkyl group, and still more preferably a C1-C4 linear alkyl group.

Specific examples of the C1-C8 linear or branched alkyl group represented by $R_{10}$ in formula (a) include the same as the C1-C8 linear or branched alkyl group described in the section of the specific examples of the C1-C12 linear or branched alkyl group represented by $R_1$ and $R_4$ in formula (1). A C1-C7 linear or branched alkyl group is preferable, and a C1-C7 linear alkyl group is more preferable.

Specific examples of the C1-C8 linear or branched alkoxy group represented by $R_{10}$ in formula (a) include the same as the C1-C8 linear or branched alkoxy group described in the section of the specific examples of the C1-C12 linear or branched alkoxy group represented by $R_1$ and $R_4$ in formula (1). A C1-C7 linear or branched alkoxy group is preferable, and a C1-C7 linear alkoxy group is more preferable.

Specific examples of the C1-C8 linear or branched alkyl group represented by $R_{11}$ in formula (b) include the same as the C1-C8 linear or branched alkyl group described in the section of the specific examples of the C1-C12 linear or branched alkyl group represented by $R_1$ and $R_4$ in formula (1). A C1-C5 linear or branched alkyl group is preferable, and a C1-C5 linear alkyl group is more preferable.

$R_9$ in formula (1) is preferably a C1-C12 linear or branched alkyl group.

$R_1$ in formula (1) is preferably a hydrogen atom, a C1-C12 linear or branched alkyl group, a C1-C12 linear or branched alkoxy group, a fluorine atom, a chlorine atom, —$CO_2R_9$, —$COR_9$, a cyano group, or a trifluoromethyl group. $R_1$ is more preferably a hydrogen atom, a C1-C12 linear or branched alkyl group, a fluorine atom. —$CO_2R_9$, —$COR_9$, a cyano group, or a trifluoromethyl group, still more preferably a hydrogen atom, a fluorine atom, —$CO_2R_9$, —$COR_9$, a cyano group, or a trifluoromethyl group, and particularly preferably a hydrogen atom, a fluorine atom. —$CO_2R_9$, —$COR_9$, or a cyano group.

Ra in formula (1) is preferably a hydrogen atom, a C1-C12 linear or branched alkyl group, a C1-C12 linear or branched alkoxy group, a fluorine atom, a chlorine atom, —$CO_2R_9$, —$COR_9$, a cyano group, or a trifluoromethyl group. $R_4$ is more preferably a hydrogen atom, a C1-C12 linear or branched alkyl group, a fluorine atom, —$CO_2R_9$, —$COR_9$, a cyano group, or a trifluoromethyl group, still more preferably a hydrogen atom, a C1-C12 linear or branched alkyl group, a fluorine atom, —$CO_2R_9$, —$COR_9$, or a cyano group, particularly preferably a C1-C12 linear or branched alkyl group, and most preferably a C4-C8 linear or branched alkyl group.

Specific examples of the C1-C4 linear or branched alkyl group represented by $R_2$, $R_3$, $R_5$, and $R_6$ in formula (1) include the same as the C1-C4 linear or branched alkyl group described in the section of the specific examples of the C1-C12 linear or branched alkyl group represented by $R_1$ and $R_4$ in formula (1). A methyl group or an ethyl group is preferable.

Specific examples of the C1-C4 linear or branched alkoxy group represented by $R_2$, $R_3$, $R_5$, and $R_6$ in formula (1) include the same as the C1-C4 linear or branched alkoxy group described in the section of the specific examples of the C1-C12 linear or branched alkoxy group represented by $R_1$ and $R_4$ in formula (1). A methoxy group or an ethoxy group is preferable.

Specific examples of the halogen atom represented by $R_2$, $R_3$, $R_5$, and $R_6$ in formula (1) include the same as the specific examples of the halogen atom represented by $R_1$ and $R_4$ in formula (1). A fluorine atom or a chlorine atom is preferable, and a fluorine atom is more preferable.

$R_2$ and $R_5$ in formula (1) are each independently preferably a hydrogen atom, a C1-C4 linear or branched alkyl group, a C1-C4 linear or branched alkoxy group, a fluorine atom, a chlorine atom, —$CO_2R_9$, —$COR_9$, a cyano group, or a trifluoromethyl group. $R_2$ and $R_5$ are each independently more preferably a hydrogen atom, a C1-C4 linear or branched alkyl group, a fluorine atom, a chlorine atom, —$CO_2R_9$, —$COR_9$, a cyano group, or a trifluoromethyl group, each independently still more preferably a hydrogen atom, a C1-C4 linear or branched alkyl group, a fluorine atom, —$CO_2R_9$, —$COR_9$, or a cyano group, each independently particularly preferably a hydrogen atom, a fluorine atom, —$CO_2R_9$, —$COR_9$, or a cyano group, and most preferably a hydrogen atom.

$R_3$ and $R_6$ in formula (1) are each independently preferably a hydrogen atom, a C1-C4 linear or branched alkyl group, a C1-C4 linear or branched alkoxy group, a fluorine atom, a chlorine atom, —$CO_2R_9$, —$COR_9$, a cyano group, or a trifluoromethyl group. $R_3$ and $R_6$ are each independently more preferably a hydrogen atom, a C1-C4 linear or branched alkyl group, a fluorine atom, a chlorine atom, —$CO_2R_9$, —$COR_9$, a cyano group, or a trifluoromethyl group, each independently still more preferably a hydrogen atom, a C1-C4 linear or branched alkyl group, a fluorine atom. —CO$_2$R$_9$, —COR$_9$, or a cyano group, and each independently particularly preferably a hydrogen atom, a fluorine atom, —CO$_2$R, —COR$_9$, or a cyano group.

Specific examples of the C1-C12 linear or branched alkyl group represented by R$_7$ and R$_8$ in formula (1) include the same as the specific examples of the C1-C12 linear or branched alkyl group represented by R$_1$ and R$_4$ in formula (1). Among them, a C4-C12 linear or branched alkyl group is preferable, and a C4-C12 linear alkyl group is more preferable.

Specific examples of the C1-C12 linear or branched alkoxy group represented by R$_7$ and R$_8$ in formula (1) include the same as the specific examples of the C1-C12 linear or branched alkoxy group represented by R$_1$ and R$_4$ in formula (1). Among them, a C4-C12 linear or branched alkoxy group is preferable, and a C4-C12 linear alkoxy group is more preferable.

R$_7$ and R$_8$ in formula (1) are each independently preferably a C4-C10 linear or branched alkyl group or a C4-C10 linear or branched alkoxy group. R$_7$ and R$_8$ are each independently more preferably a C4-C10 linear alkyl group or a C4-C10 alkoxy group, and each independently still more preferably a C4-C10 linear alkoxy group.

In formula (1), the number of substituents of the phenyl group having R$_1$ to R$_3$, and the number of substituents of the phenyl group having R$_4$ to R$_6$ are each independently preferably 0 to 2 (that is, at least one of R$_1$ to R$_3$ is a hydrogen atom, and at least one of R$_4$ to R$_6$ is a hydrogen atom), and more preferably 0 to 1 (that is, at least two of R$_1$ to R$_3$ are a hydrogen atom, and at least two of R$_4$ to R$_6$ are a hydrogen atom). It is noted that the substituent referred to herein means a group other than a hydrogen atom.

In formula (1), the position of the substituent on the phenyl group having R$_1$ to R$_3$ and the position of the substituent on the phenyl group having R$_4$ to R$_6$ are each independently preferably the 2-position alone, the 3-position alone, the 4-position alone, two positions of the 2-position and the 4-position, or two positions of the 3-position and the 4-position, more preferably the 2-position alone, the 3-position alone, or the 4-position alone, and still more preferably the 4-position alone, when described with the numbers shown in the following formula (3). For example, the 4-position alone means that only the 4-position has a substituent other than a hydrogen atom.

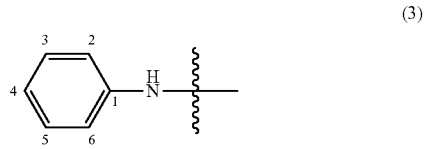

(3)

At least one of R$_1$ to R$_6$ in formula (1) is preferably a halogen atom, —CO$_2$R$_9$, —COR$_9$, a cyano group, or a trifluoromethyl group.

As R$_1$ and R$_3$ in formula (1), only one of R$_1$ and R$_3$ is preferably a hydrogen atom, and only R$_3$ is more preferably a hydrogen atom, and/or as R$_4$ and R$_6$ in formula (1), only one of R$_4$ and R$_6$ is preferably a hydrogen atom, and only R$_6$ is more preferably a hydrogen atom.

The anthraquinone compound represented by formula (1) is more preferably a combination of preferred to most preferred embodiments of each of R$_1$ to R$_9$ described above. R$_{10}$ in formula (a), and R$_{11}$ in formula (b).

Preferable specific examples of the compound represented by formula (1) include the following compounds, but the present invention is not limited thereto.

The alkyl group, the alkyl moiety of the alkoxy group, and the alkyl moiety of the ester group in the structures of the following specific examples all have a linear carbon chain.

No. 1

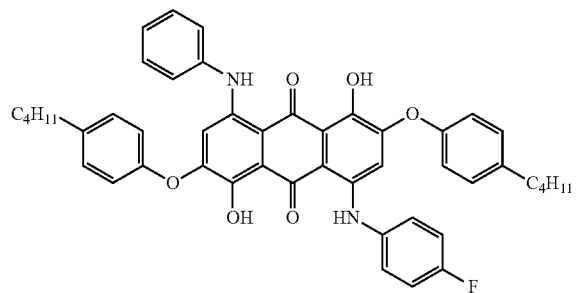

No. 2

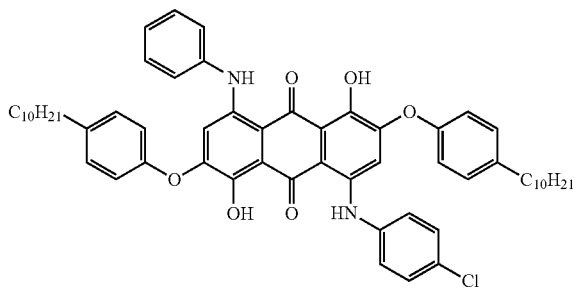

No. 3

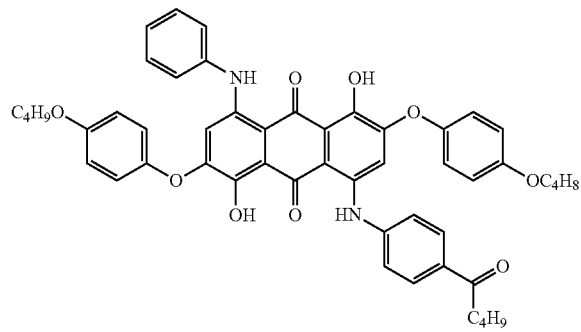

No. 4

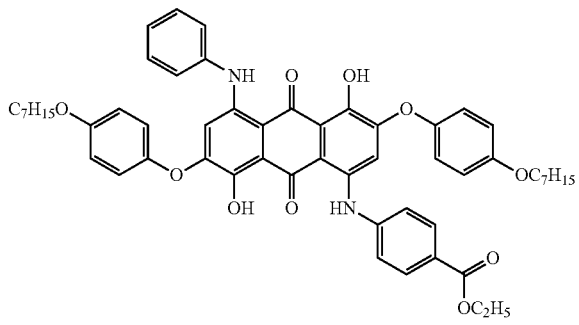

-continued
No. 5
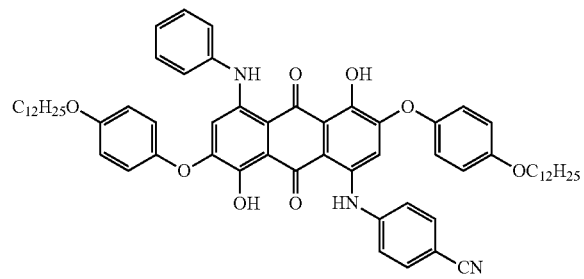
No. 6
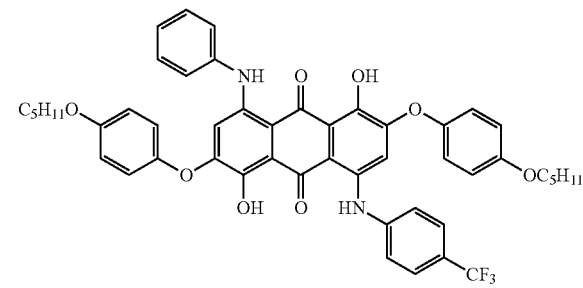
No. 7
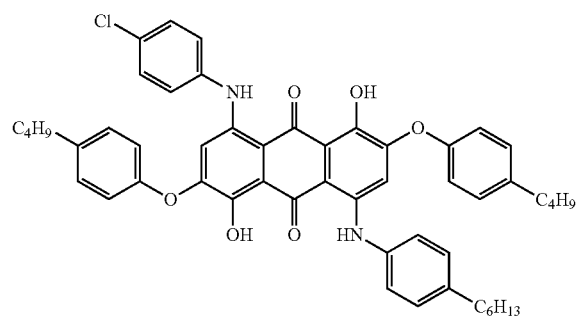
No. 8
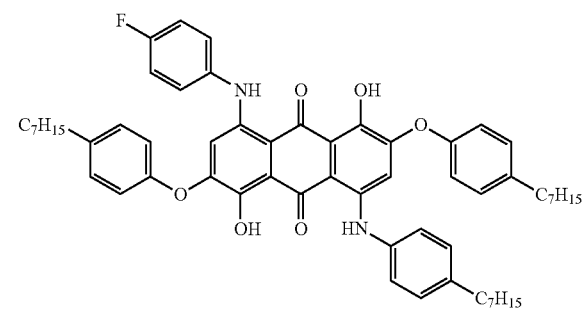
No. 9
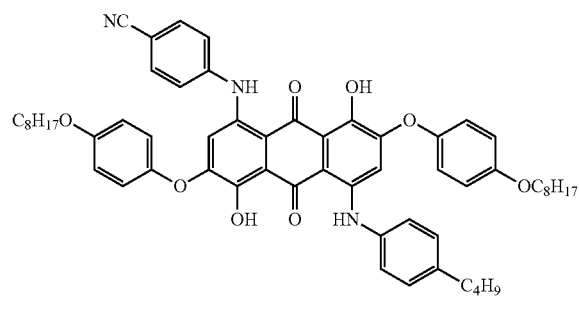
No. 10
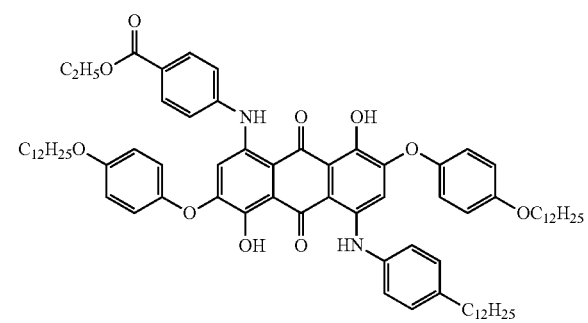
No. 11
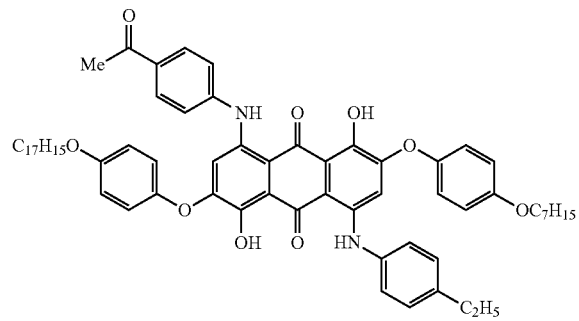
No. 12
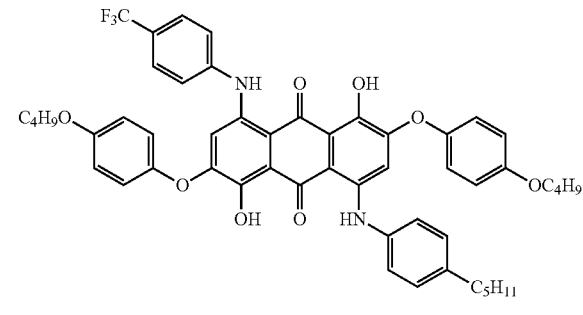

No. 13
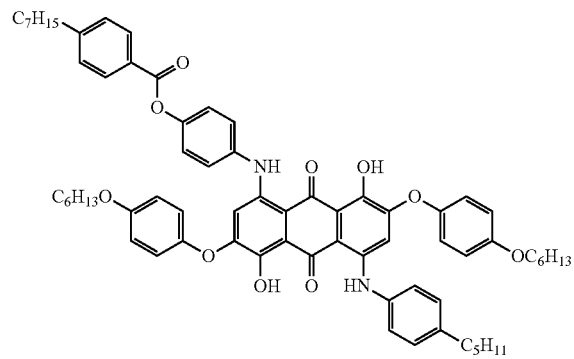
No. 14
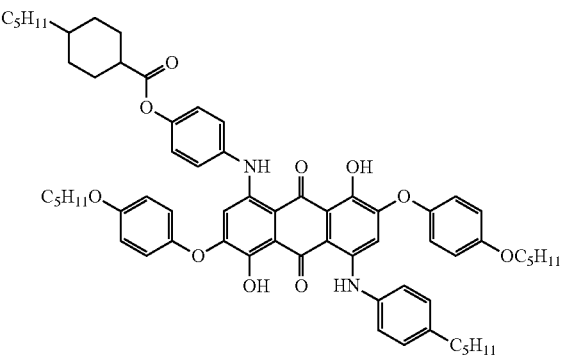
No. 15
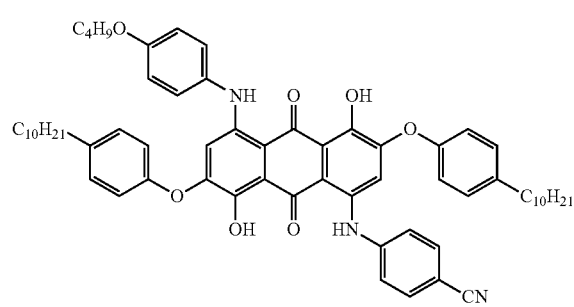
No. 16
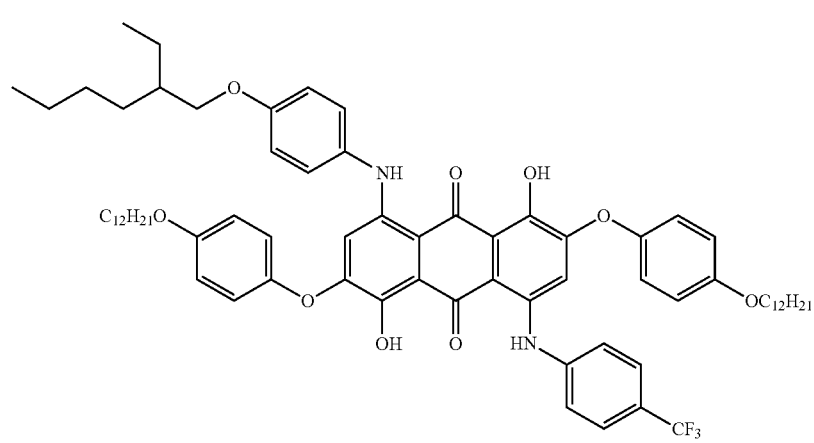
No. 17
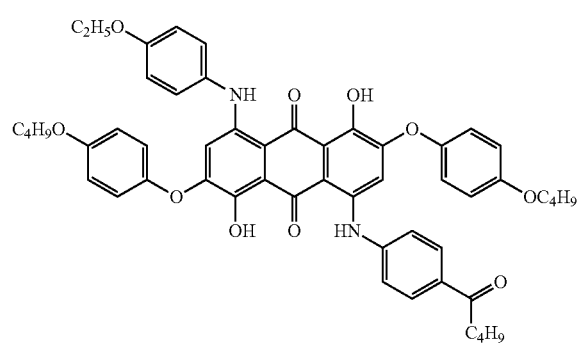

-continued
No. 18
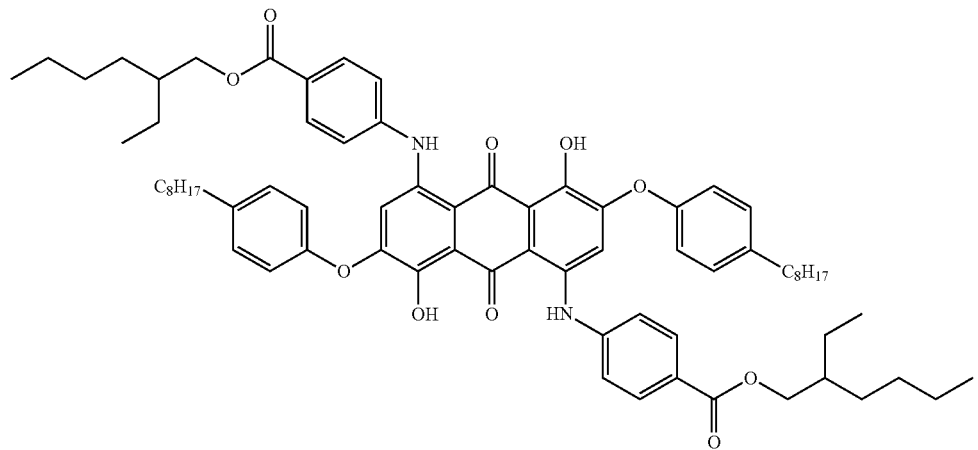
No. 19
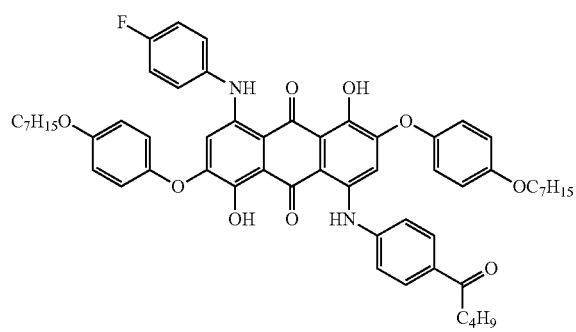
No. 20
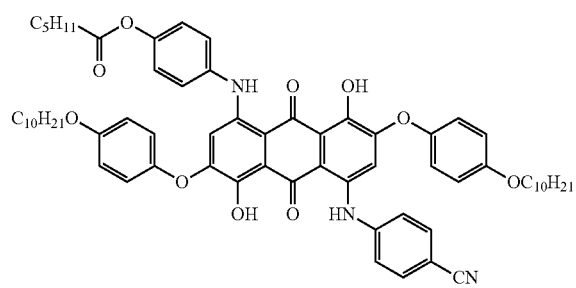
No. 21
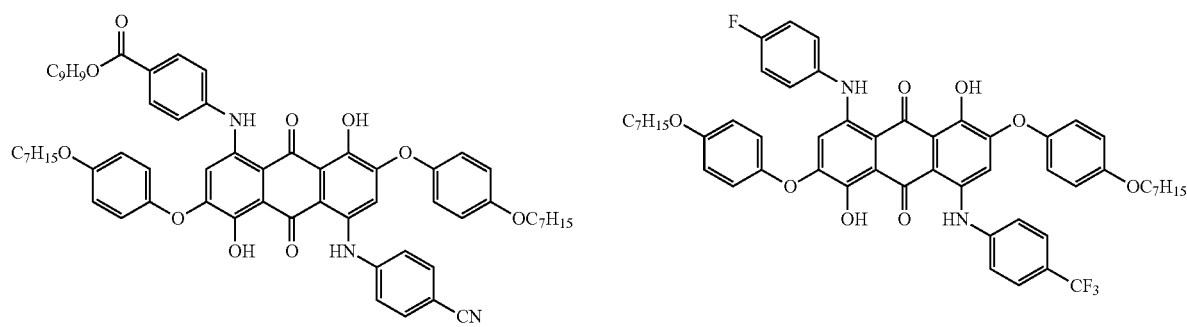
No. 22
No. 23
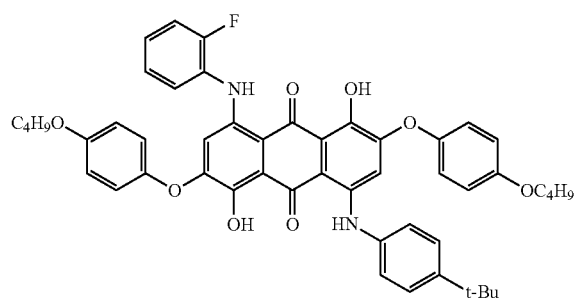
No. 24
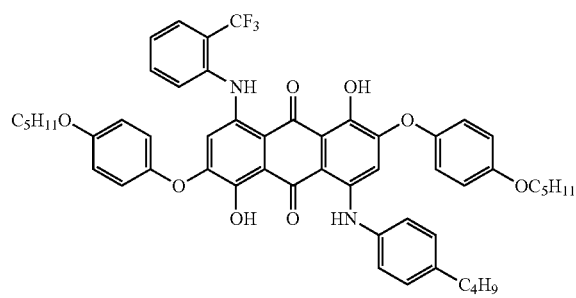

-continued
No. 25
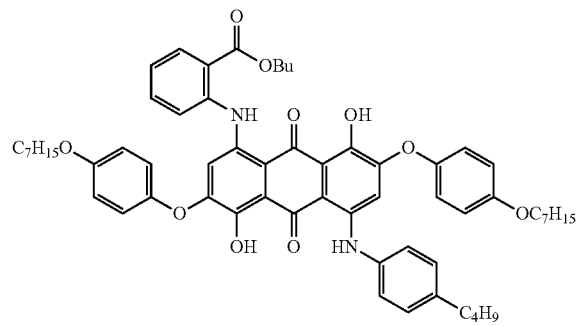
No. 26
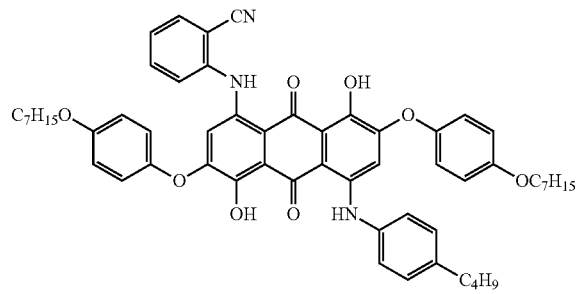
No. 27
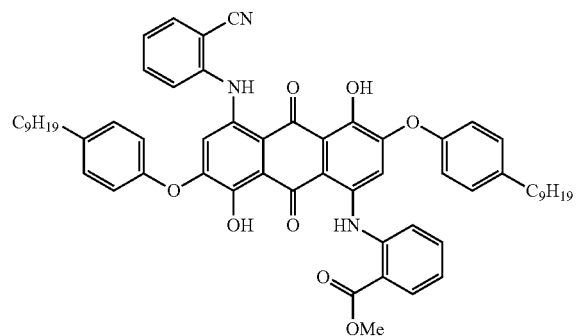
No. 28
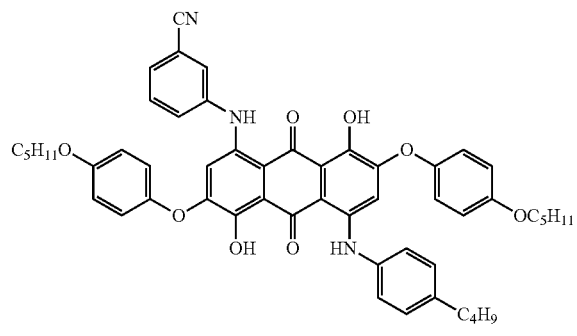
No. 29
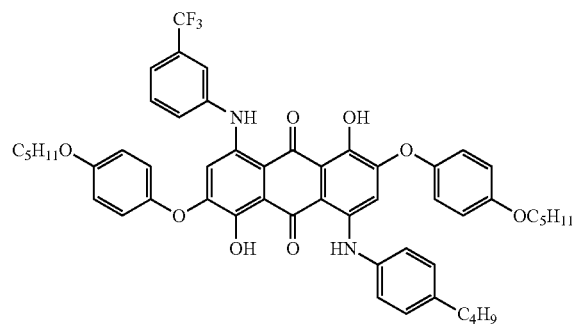
No. 30
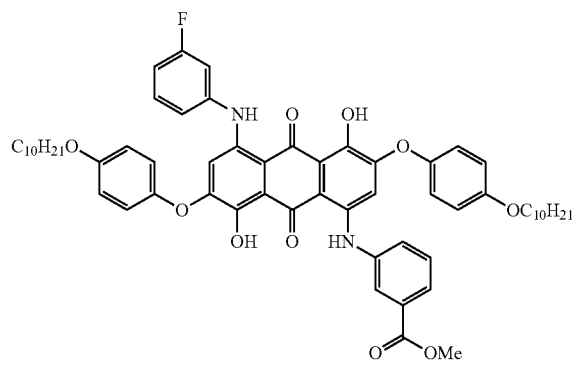
No. 31
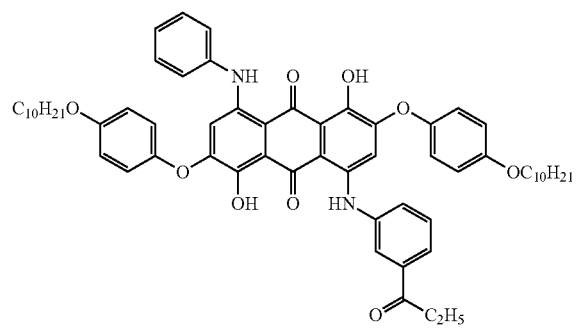
No. 32
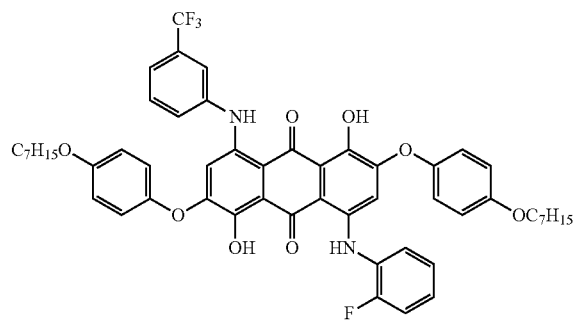

-continued
No. 33
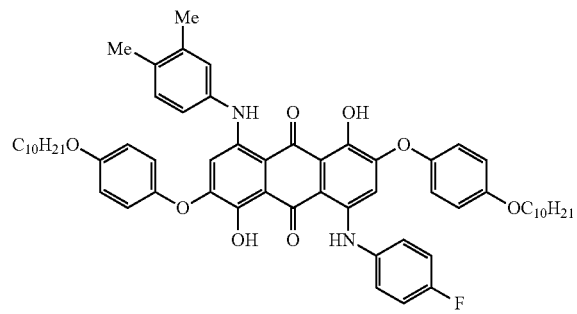
No. 34
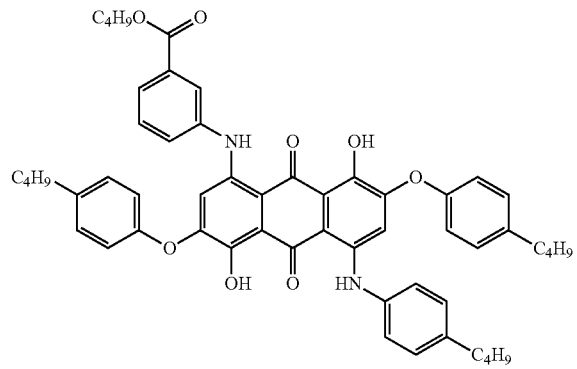
No. 35
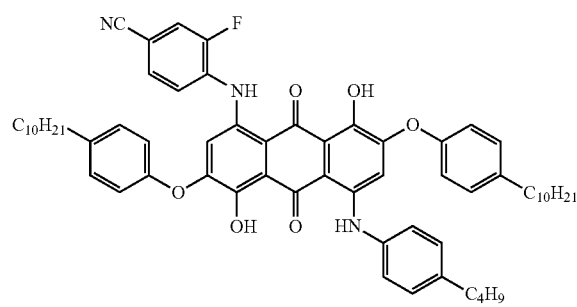
No. 36
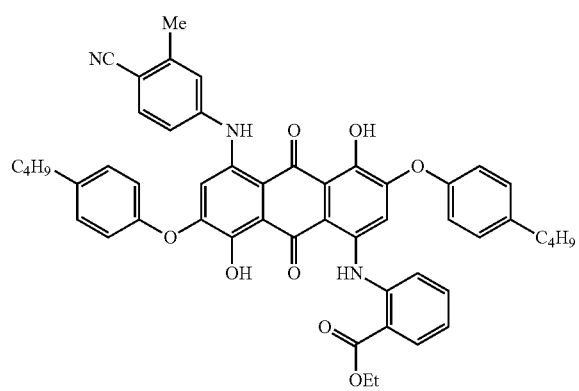
No. 37
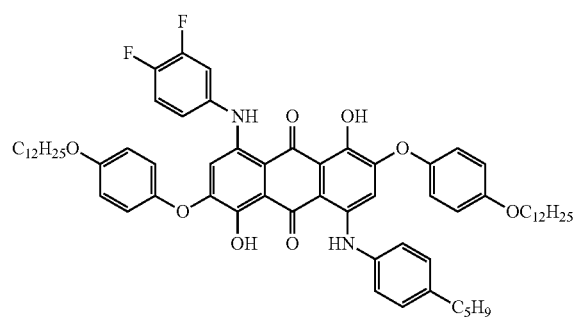
No. 38
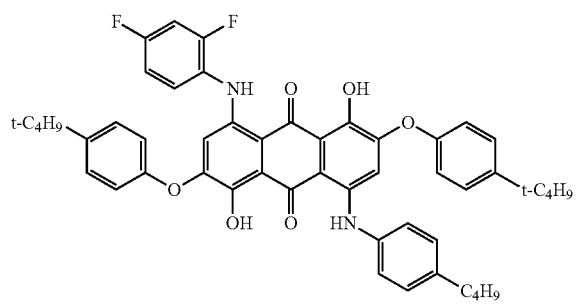
No. 39
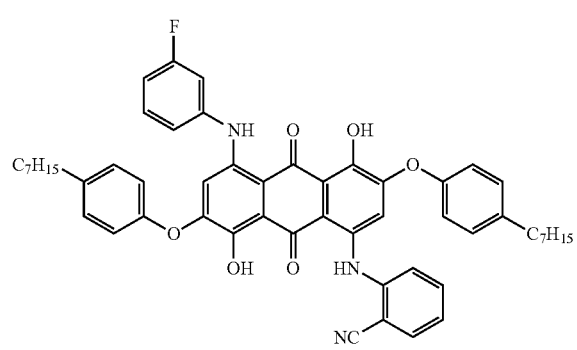
No. 40
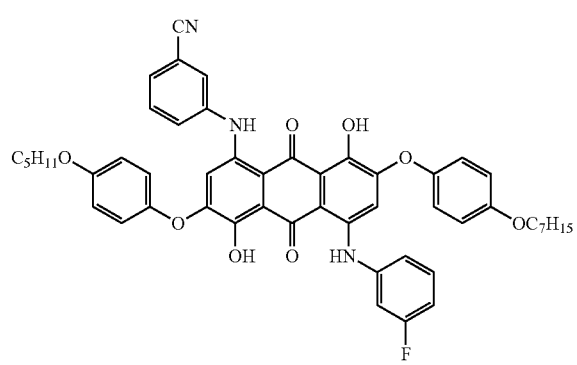

-continued
No. 41
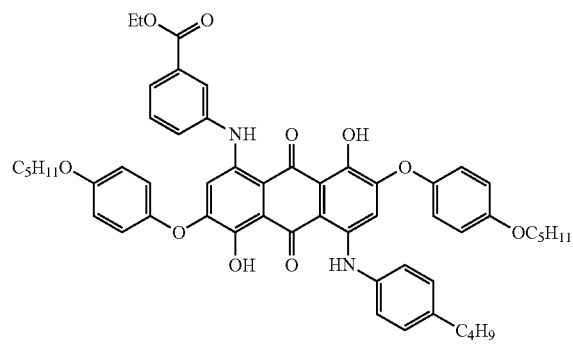
No. 42
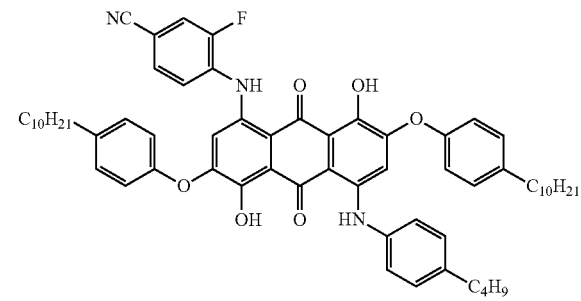
No. 43
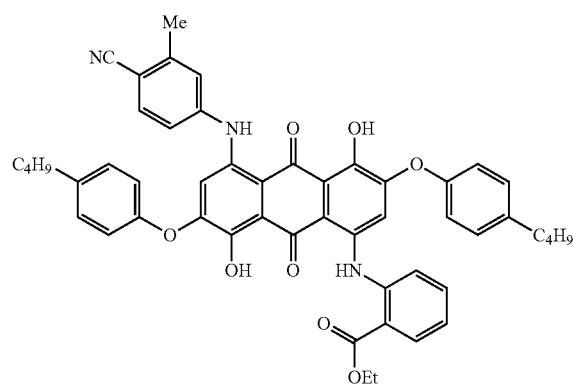
No. 44
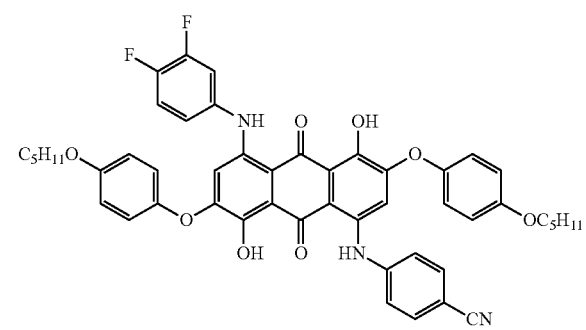
No. 45
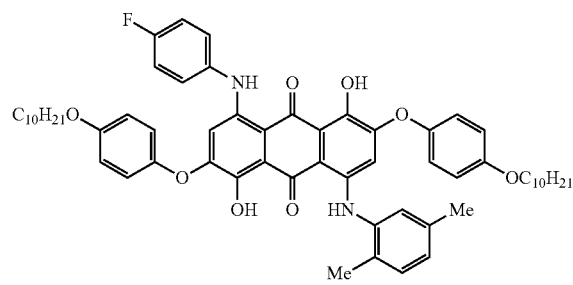
No. 46
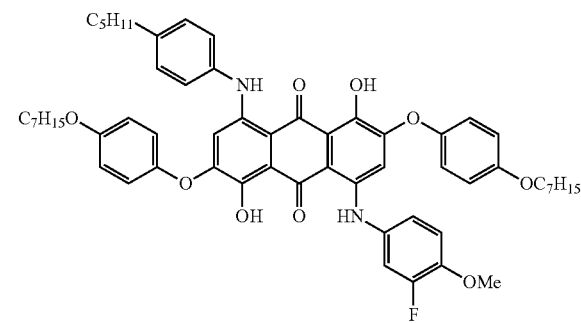
No. 47
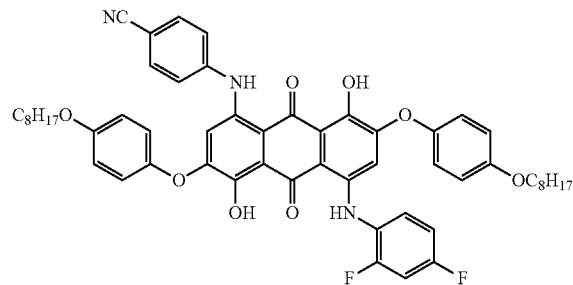
No. 48
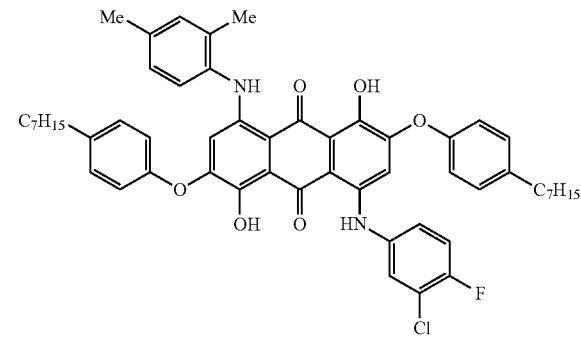

-continued

No. 49
No. 50
No. 51
No. 52
No. 53
No. 54

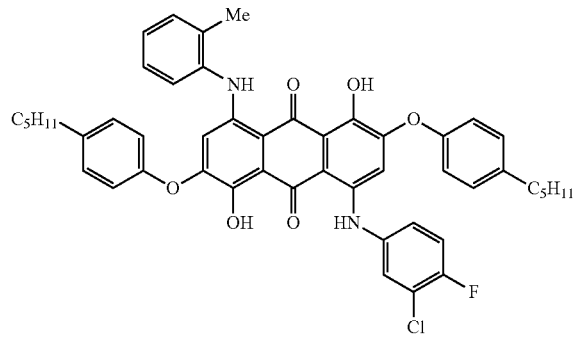
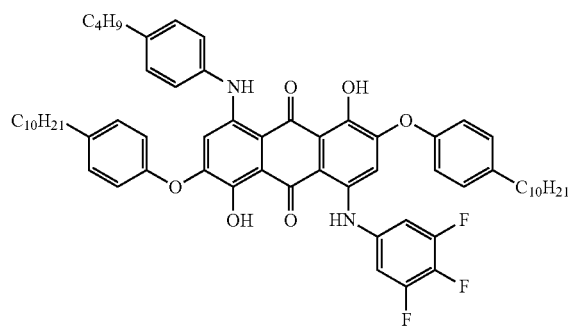
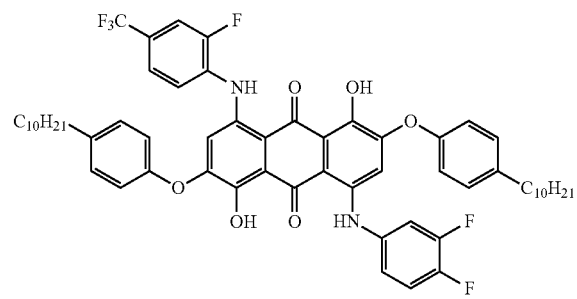
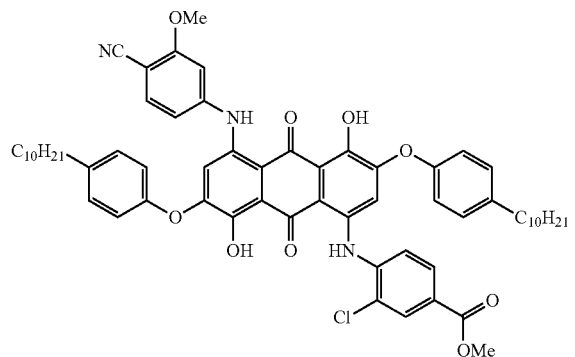

The anthraquinone compound represented by formula (1) of the present invention can be synthesized with reference to, for example, the method described in US 2004/0087692 A1.

Specifically, for example, the anthraquinone compound can be synthesized by reacting an anthraquinone compound represented by the following formula (A), which is synthesized by a conventionally known method described in JP-A-63-72760 or the like, with an iodobenzene derivative represented by the following formula (B) (or alternatively a bromobenzene derivative) at 140 to 160° C. in a solvent such as N-methyl-2-pyrrolidone in the presence of a copper catalyst such as a copper powder under basic conditions such as potassium carbonate.

It is noted that $R_1$ to $R_8$ in the following formulas (A) and (B) have the same meaning as in formula (I). As another method of this synthesis method, instead of the reaction of introducing, as an iodobenzene derivative, a benzene ring having $R_1$ to $R_3$ as substituents (for example, the reaction exemplified in Examples 1 to 3 described below), a reaction of introducing, as an iodobenzene derivative, a benzene ring having $R_4$ to $R_6$ as substituents (for example, the reaction exemplified in Example 4 described below) may be performed.

(A)

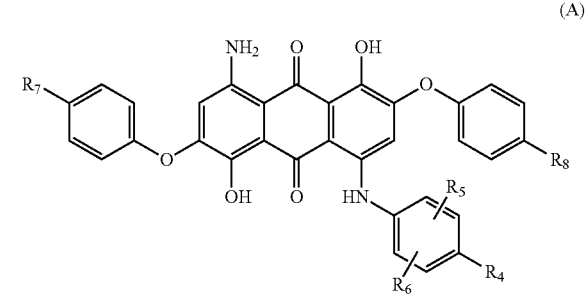

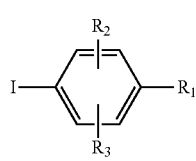
(B)

A liquid crystal composition of the present invention (hereinafter, also sometimes simply referred to as "composition of the present invention") contains the anthraquinone compound represented by formula (1) and a liquid crystal material.

The content ratio of the anthraquinone compound represented by formula (1) in the liquid crystal composition is not particularly limited, but is preferably 0.5 to 15 parts by mass and more preferably 0.5 to 5 parts by mass with respect to 100 parts by mass of the liquid crystal material. When a dichroic dye (described below) other than the compound represented by formula (1) is used in combination, the total content of the anthraquinone compound represented by formula (1) and the dichroic dye other than the compound represented by formula (1) is preferably in the above range (0.5 to 15 parts by mass) with respect to 100 parts by mass of the liquid crystal material.

The liquid crystal material contained in the liquid crystal composition of the present invention is not particularly limited as long as it is a material having liquid crystallinity (i.e., a compound having liquid crystallinity) such as nematic liquid crystal, cholesteric liquid crystal, or smectic liquid crystal, but among them, nematic liquid crystal is preferable. Examples of the compound having liquid crystallinity include liquid crystal compounds described in pages 154 to 192 and pages 715 to 722 of "Liquid Crystal Device Handbook" (edited by the 142nd Committee of the Japan Society for the Promotion of Science, THE NIKKAN KOGYO SHIMBUN, LTD., 1989).

The liquid crystal composition of the present invention may contain a dichroic dye other than the anthraquinone compound represented by formula (1), or an optically active substance that shows or does not show a liquid crystal phase such as a cholesteryl nonanoate, additives such as an ultraviolet absorber and an antioxidant, a photocurable compound, a photopolymerization initiator, and the like.

The photocurable compound that can be contained in the liquid crystal composition of the present invention is not particularly limited as long as it is a compound having a functional group capable of being polymerized by the action of a photopolymerization initiator described below when irradiated with light. Examples of the photocurable compound include a compound having a (meth)acrylate group, a compound having a vinyl group, and a compound having an allyl group. A compound having a (meth)acrylate group is preferable. It is noted that the term "(meth)acrylate" referred to herein means "methacrylate and/or acrylate".

Examples of the (meth)acrylate compound contained in the liquid crystal composition of the present invention include, but are not limited to, a mono(meth)acrylate compound having one (meth)acrylate group in one molecule and a di(meth)acrylate compound having two (meth)acrylate groups in one molecule.

The mono(meth)acrylate compound is preferably a mono(meth)acrylate having a C5-C13 linear, cyclic, or branched alkyl group. Specific examples thereof include linear alkyl mono(meth)acrylates such as pentyl (meth)acrylate, hexyl (meth)acrylate, heptyl (meth)acrylate, octyl (meth)acrylate, nonyl (meth)acrylate, decyl (meth)acrylate, undecyl (meth)acrylate, dodecyl (meth)acrylate, and tridecyl (meth)acrylate; cyclic alkyl mono(meth)acrylates such as isobornyl (meth)acrylate; and branched alkyl mono(meth)acrylates such as 2-methylhexyl (meth)acrylate, 2-ethylhexyl (meth)acrylate, 2-propylhexyl (meth)acrylate, 2-methylheptyl (meth)acrylate, 2-ethylheptyl (meth)acrylate, and 2-propylheptyl (meth)acrylate.

Examples of the di(meth)acrylate compound include 1,4-butanediol di(meth)acrylate, 1,5-pentanediol di(meth)acrylate, 1,6-hexanediol di(meth)acrylate, 1,7-heptanediol di(meth)acrylate, 1,8-octanediol di(meth)acrylate, 1,9-nonanediol di(meth)acrylate, 1,10-decanediol di(meth)acrylate, 1,11-undecanediol di(meth)acrylate, 1,12-dodecanediol di(meth)acrylate, and 1,13-tridecanediol di(meth)acrylate, and further include trialkylene glycol di(meth)acrylates such as triethylene glycol di(meth)acrylate.

In the liquid crystal composition of the present invention, the mono(meth)acrylate compound and the di(meth)acrylate compound may be used in combination. When the mono(meth)acrylate compound and the di(meth)acrylate compound are used in combination, the mass ratio of the mono(meth)acrylate compound to the di(meth)acrylate compound is preferably 10:90 to 96:4 and more preferably 50:0 to 95:5.

The photopolymerization initiator that can be contained in the composition of the present invention is not particularly limited as long as it is a compound capable of polymerizing a photocurable compound(s) by light irradiation. The photopolymerization initiator is preferably one that does not remain in the cured product after light irradiation and does not cause deterioration of the dichroic dye such as the anthraquinone compound represented by formula (1).

As the photopolymerization initiator, for example, alkylphenone-based photopolymerization initiators such as DAROCURE 1173. IRGACURE 651, and IRGACURE 184, and phosphine oxide-based photopolymerization initiators such as IRGACURE TPO are preferably used.

In the composition of the present invention when containing the photocurable compound and the photopolymerization initiator, the blending ratio of the total of the anthraquinone compound represented by formula (1) and the liquid crystal material to the photocurable compound is preferably 90:10 to 50:50, more preferably 80:20 to 50:50, and still more preferably 60:40 to 50:50 in mass ratio. When the blending ratio of the photocurable compound is set in the above range, it is possible to prevent separation of the liquid crystal material and the photocurable compound before curing by light irradiation and deterioration of the light shielding property of the cured product.

In the case of using a dichroic dye (described below) other than the compound represented by formula (1) in combination, the blending ratio of the total of the entire dichroic dye containing the anthraquinone compound represented by formula (1) and the liquid crystal material to the photocurable compound in the composition of the present invention is preferably in the above range (90:10 to 50:50 in mass ratio), and the more preferred range and the still more preferred range are also the same as those described above.

The content of the photopolymerization initiator in the composition of the present invention when containing the photocurable compound and the photopolymerization initiator is preferably 0.1 to 5 parts by mass with respect to 100 parts by mass of the photocurable compound.

A dichroic dye other than the anthraquinone compound represented by formula (1) can be used in combination in the composition of the present invention.

The dichroic dye that can be used in combination is not particularly limited, and may be selected from, for example, an azo dye, an anthraquinone dye, a perylene dye, a quinophthalone dye, a merocyanine dye, an azomethine dye, a phthaloperylene dye, an indigo dye, an azulene dye, a dioxazine dye, a polythiophene dye, and the like. Specific examples thereof include those described in "Dichroic dyes for Liquid Crystal Display" (A. V. Ivashchenko, C R C, 1994).

Among them, an azo dye, an anthraquinone dye, a perylene dye, or a quinophthalone dye is preferably used in combination, and an azo dye or an anthraquinone dye is more preferably used in combination.

In the case of using a dichroic dye other than the anthraquinone compound represented by formula (1) in combination, the content of the anthraquinone compound represented by formula (1) in the entire dichroic dye is not particularly limited as long as the effect of the present invention is not impaired. The amount thereof is preferably 1 to 80 mass %, more preferably 5 to 70 mass %, and still more preferably 10 to 50 mass %.

In the composition of the present invention, light stabilizers such as benzotriazole-based, benzophenone-based, and hindered amine-based light stabilizers, antioxidants such as phosphite-based and hindered phenol-based antioxidants, a thermal polymerization inhibitor, a thiol compound, a photosensitizing agent, a photosensitizer, a chain transfer inhibitor, a polymerization inhibitor, an adhesiveness imparting agent, an antifoaming agent, a crosslinking agent, a surfactant, a thermosetting accelerator, a thermoplastic resin, a thermosetting resin, a thickener such as a urethane diacrylate, and the like may be further used in combination.

In order to control a cell gap as the light control element, a spherical or cylindrical spacer, such as silica, glass, plastics, or ceramics, may be added. The cell gap in this case can be set in a range of 2 to 100 µm.

The composition of the present invention can be obtained by mixing and stirring the anthraquinone compound represented by formula (1) and the liquid crystal material, which are essential components, and other optional components, such as the photocurable compound and the photopolymerization initiator, as necessary. The mixing and stirring may be performed, in the simplest way, by placing all the constituent components in a container and manually stirring them, but it is effective to stir them using equipment such as a magnetic stirrer. In order to efficiently prepare a uniform composition, it is preferable to first prepare a uniform mixture of the photocurable compound, the photopolymerization initiator, and the liquid crystal material, then add the anthraquinone compound represented by formula (1) and other optional components, and stir and mix them. During stirring and mixing, heating may be performed as necessary. The stirring and mixing under a light source emitting an absorption wavelength of the photopolymerization initiator are preferably performed in as short a time as possible. After mixing the components, filtration may be further performed using a mesh, a membrane filter, or the like.

When the composition of the present invention containing the photocurable compound and the photopolymerization initiator is irradiated with light, a cured product of the liquid crystal composition, in which the photocurable compound component is cured (polymerized), can be obtained. Note that the "cured product" in the present invention means a state where the functional group of the photocurable compound is polymerized or copolymerized by light irradiation, and does not necessarily mean a cured product in which the anthraquinone compound represented by formula (1), the liquid crystal material, or the like has contributed to the curing reaction.

A light source for the light irradiation is not particularly limited as long as it is a light source capable of emitting light having a wavelength to be absorbed by the photopolymerization initiator. Preferable examples of the light source include high-pressure mercury lamp, a metal halide lamp, a xenon lamp, and a halogen lamp that are capable of emitting ultraviolet rays.

In the light control element of the present invention, a layer of the liquid crystal composition or a photocured product thereof is sandwiched between a pair of substrates disposed opposite to each other, at least one of which is a transparent substrate having a transparent electrode. Here, examples of the substrate include a colorless transparent, colored transparent, or opaque substrate such as an inorganic transparent material such as glass or quartz, a metal, a metal oxide, a semiconductor, ceramics, a plastic plate, or a plastic film. The electrode is formed on the substrate by, for example, forming a thin film of a metal oxide, a metal, a semiconductor, an organic conductive material, or the like on the entire surface or a part of the substrate by a known coating method, a printing method, a vapor deposition method such as sputtering, or the like. In particular, in order to obtain a light control element having a large area, it is desirable to use an electrode substrate in which an ITO (indium oxide, tin oxide) electrode is formed on a transparent polymer film such as PET using a vapor deposition method such as sputtering, a printing method, or the like from the viewpoints of productivity and processability. It is a more preferable embodiment that both of the pair of substrates are transparent substrates having a transparent electrode. Wiring may be provided on the substrate for connecting between the electrodes or between the electrodes and the outside. For example, a segment driving electrode substrate, a matrix driving electrode substrate, an active matrix driving electrode substrate, or the like may be used. The surface of the electrode provided on the substrate may be entirely or partially covered with a protective film or an alignment film made of an organic compound such as a polyimide, a polyamide, silicon, or a cyan compound, an inorganic compound such as $SiO_2$, $TiO_2$, or $ZrO_2$, or a mixture thereof.

By using the plastic film as a substrate, a flexible and lightweight light control element can be obtained. Therefore, it is possible to use the light control element by sandwiching the light control element between a pair of planar or curved substrates of glass, hard plastic, or the like with an adhesive layer such as polyvinyl butyral, vinyl acetate, a double-sided tape, or an adhesive. Alternatively, the light control element can be used by being attached to the surface of one planar or curved substrate of glass, hard plastic, or the like with a double-sided tape, an adhesive, or the like. Alternatively, the light control element may be sandwiched between soft plastic substrates or be attached to one side or both sides. A protective layer such as a hard coat, an ultraviolet rays cut layer, an infrared rays cut layer, or a half mirror may be provided on the substrate surface opposite to the electrode surface of the light control element, or a color filter may be laminated on the light control element or a polarizer filter may be attached to the light control element. Alternatively, the light control element may be laminated with an electroluminescence display element, a light emitting diode display element, an electrochromic display element, or another liquid crystal display element.

A drive device for applying a voltage to the light control element of the present invention is a device capable of applying a DC voltage of 2 to 100 V or an AC voltage of 10 to 1000 Hz, and may be a device that opens or short-circuits between electrodes when no voltage is applied. This drive device may include a voltage application circuit for segment driving, a voltage application circuit for matrix driving, a voltage application circuit for active matrix, and the like.

The anthraquinone compound represented by formula (1) of the present invention has high light resistance, and a light control element using this anthraquinone compound can realize high quality display with little color change over a long period of time. Since the light control element of the present invention is excellent in light resistance due to long-term outdoor exposure of light at a high temperature, the light control element is optimal for vehicle-mounted applications or building material applications.

EXAMPLES

Hereinafter, the present invention will be described in more detail with reference to Examples; however, the present invention is not limited thereto. It is noted that the terms "part(s)" and "%" in the present text are on amass basis unless otherwise specified. The maximum absorption wavelength in Examples is a value measured with a spectrophotometer "UV-3150" manufactured by SHIMADZU CORPORATION.

Example 1 (Synthesis of Anthraquinone Compound of Present Invention Represented by No. 8 in Specific Compound Examples)

To 20 parts of NMP, 0.9 parts of a compound represented by the following formula (11), 0.02 parts of copper powder, 0.02 parts of copper iodide, 2.0 parts of 1-fluoro-4-iodobenzene, 0.02 parts of potassium carbonate, and 0.15 parts of sodium acetate were added, the mixture was stirred at 140 to 150° C. for 12 hours, the reaction solution was then cooled to 25° C., 200 parts of methanol was added, and the mixture was further stirred for 1 hour. The reaction product was collected by filtration, washed with methanol, and then dried in a hot air dryer at 50° C. for 24 hours. The obtained crude product was dissolved in toluene, and column purification was performed using toluene as a developing solvent. The solvent was distilled off under reduced pressure from the solution after purification, and the resultant was dried in a hot air dryer at 50° C. for 24 hours to obtain 0.2 parts of the compound represented by No. 8 in the above specific compound examples as a dark brown solid. The maximum absorption wavelength of this compound in toluene was 651 nm.

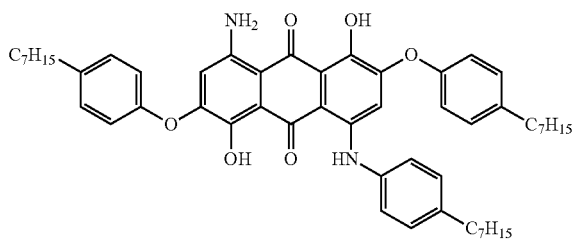

(11)

Example 2 (Synthesis of Anthraquinone Compound of Present Invention Represented by No. 9 in Specific Compound Examples)

To 20 parts of NMP, 0.9 parts of a compound represented by the following formula (12), 0.02 parts of copper powder, 0.02 parts of copper iodide, 2.0 parts of 4-iodobenzonitrile, 0.02 parts of potassium carbonate, and 0.15 parts of sodium acetate were added, the mixture was stirred at 140 to 150° C. for 12 hours, the reaction solution was then cooled to 25° C., 200 parts of methanol was added, and the mixture was further stirred for 1 hour. The reaction product was collected by filtration, washed with methanol, and then dried in a hot air dryer at 50° C. for 24 hours. The obtained crude product was dissolved in toluene, and column purification was performed using toluene as a developing solvent. The solvent was distilled off under reduced pressure from the solution after purification, and the resultant was dried in a hot air dryer at 50° C. for 24 hours to obtain 0.15 parts of the compound represented by No. 9 in the above specific compound examples as a dark brown solid. The maximum absorption wavelength of this compound in toluene was 650 nm.

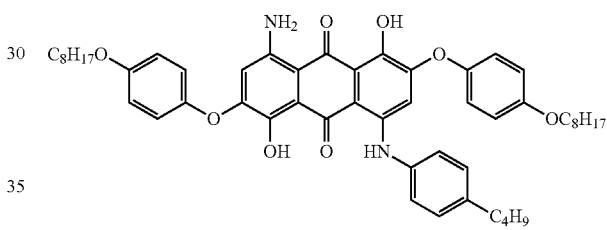

(12)

Example 3 (Synthesis of Anthraquinone Compound of Present Invention Represented by No. 10 in Specific Compound Examples)

To 20 parts of NMP, 0.9 parts of a compound represented by the following formula (13), 0.02 parts of copper powder, 0.02 parts of copper iodide, 2.0 parts of ethyl 4-iodobenzoate, 0.02 parts of potassium carbonate, and 0.15 parts of sodium acetate were added, the mixture was stirred at 140 to 150° C. for 12 hours, the reaction solution was then cooled to 25° C., 200 parts of methanol was added, and the mixture was further stirred for 1 hour. The reaction product was collected by filtration, washed with methanol, and then dried in a hot air dryer at 50° C. for 24 hours. The obtained crude product was dissolved in toluene, and column purification was performed using toluene as a developing solvent. The solvent was distilled off under reduced pressure from the solution after purification, and the resultant was dried in a hot air dryer at 50° C. for 24 hours to obtain 0.18 parts of the compound represented by No. 10 in the above specific compound examples as a dark brown solid. The maximum absorption wavelength of this compound in toluene was 655 nm.

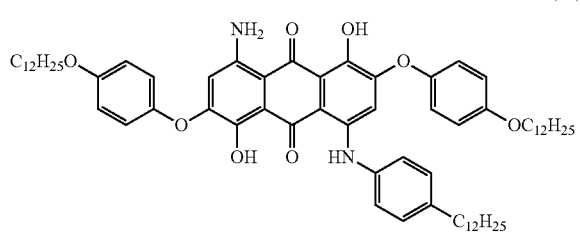
(13)

Example 4 (Synthesis of Anthraquinone Compound of Present Invention Represented by No. 19 in Specific Compound Examples)

To 20 parts of NMP, 0.9 parts of a compound represented by the following formula (14), 0.02 parts of copper powder, 0.02 parts of copper iodide, 2.0 parts of 4-iodobenzonitrile, 0.02 parts of potassium carbonate, and 0.15 parts of sodium acetate were added, the mixture was stirred at 140 to 150° C. for 12 hours, the reaction solution was then cooled to 25° C., 200 parts of methanol was added, and the mixture was further stirred for 1 hour. The reaction product was collected by filtration, washed with methanol, and then dried in a hot air dryer at 50° C. for 24 hours. The obtained crude product was dissolved in toluene, and column purification was performed using toluene as a developing solvent. The solvent was distilled off under reduced pressure from the solution after purification, and the resultant was dried in a hot air dryer at 50° C. for 24 hours to obtain 0.1 parts of the compound represented by No. 19 in the above specific compound examples as a brown solid. The maximum absorption wavelength of this compound in toluene was 651 nm.

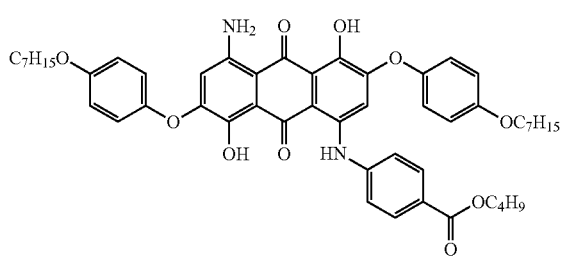
(14)

Example 5 (Synthesis of Anthraquinone Compound of Present Invention Represented by No. 5 in Specific Compound Examples)

To 20 parts of NMP, 0.9 parts of a compound represented by the following formula (15), 0.02 parts of copper powder, 0.02 parts of copper iodide, 2.0 parts of 4-iodobenzonitrile, 0.02 parts of potassium carbonate, and 0.15 parts of sodium acetate were added, the mixture was stirred at 140 to 150° C. for 12 hours, the reaction solution was then cooled to 25° C., 200 parts of methanol was added, and the mixture was further stirred for 1 hour. The reaction product was collected by filtration, washed with methanol, and then dried in a hot air dryer at 50° C. for 24 hours. The obtained crude product was dissolved in toluene, and column purification was performed using toluene as a developing solvent. The solvent was distilled off under reduced pressure from the solution after purification, and the resultant was dried in a hot air dryer at 50° C. for 24 hours to obtain 0.15 parts of the compound represented by No. 5 in the above specific compound examples as a dark brown solid. The maximum absorption wavelength of this compound in toluene was 651 nm.

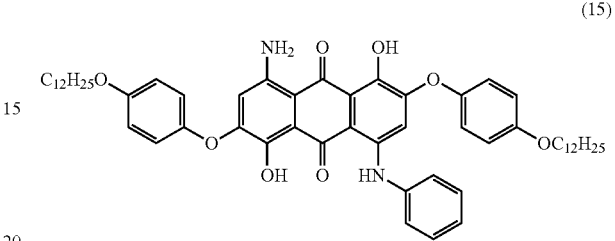
(15)

Example 6 (Synthesis of Anthraquinone Compound of Present Invention Represented by No. 7 in Specific Compound Examples)

To 20 parts of NMP, 0.9 parts of a compound represented by the following formula (16), 0.02 parts of copper powder, 0.02 parts of copper iodide, 2.5 parts of 1-chloro-4-iodobenzene, 0.02 parts of potassium carbonate, and 0.15 parts of sodium acetate were added, the mixture was stirred at 140 to 150° C. for 12 hours, the reaction solution was then cooled to 25° C., 200 parts of methanol was added, and the mixture was further stirred for 1 hour. The reaction product was collected by filtration, washed with methanol, and then dried in a hot air dryer at 50° C. for 24 hours. The obtained crude product was dissolved in toluene, and column purification was performed using toluene as a developing solvent. The solvent was distilled off under reduced pressure from the solution after purification, and the resultant was dried in a hot air dryer at 50° C. for 24 hours to obtain 0.05 parts of the compound represented by No. 7 in the above specific compound examples as a dark brown solid. The maximum absorption wavelength of this compound in toluene was 652 nm.

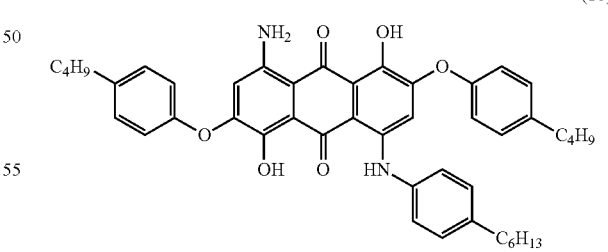
(16)

Example 7 (Synthesis of Anthraquinone Compound of Present Invention Represented by No. 11 in Specific Compound Examples)

To 20 parts of NMP, 0.9 parts of a compound represented by the following formula (17), 0.02 parts of copper powder, 0.02 parts of copper iodide, 2.0 parts of 4-iodoacetophenone, 0.02 parts of potassium carbonate, and 0.15 parts of sodium acetate were added, the mixture was stirred at 140 to 150° C. for 12 hours, the reaction solution was then cooled to 25° C., 200 parts of methanol was added, and the mixture was further stirred for 1 hour. The reaction product was collected by filtration, washed with methanol, and then dried in a hot air dryer at 50° C. for 24 hours. The obtained crude product was dissolved in toluene, and column purification was performed using toluene as a developing solvent. The solvent was distilled off under reduced pressure from the solution after purification, and the resultant was dried in a hot air dryer at 50° C. for 24 hours to obtain 0.15 parts of the compound represented by No. 11 in the above specific compound examples as a dark brown solid. The maximum absorption wavelength of this compound in toluene was 654 nm.

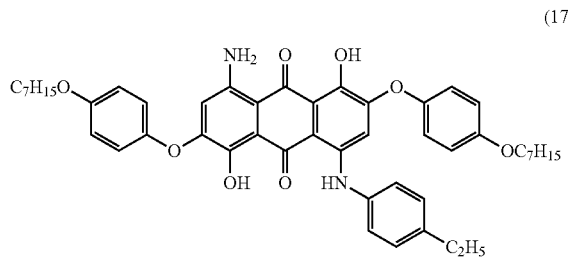

(17)

Example 8 (Synthesis of Anthraquinone Compound of Present Invention Represented by No. 12 in Specific Compound Examples)

To 20 parts of NMP, 0.9 parts of a compound represented by the following formula (18), 0.02 parts of copper powder, 0.02 parts of copper iodide, 2.0 parts of 4-iodobenzotrifluoride, 0.02 parts of potassium carbonate, and 0.15 parts of sodium acetate were added, the mixture was stirred at 140 to 150° C. for 12 hours, the reaction solution was then cooled to 25° C., 200 parts of methanol was added, and the mixture was further stirred for 1 hour. The reaction product was collected by filtration, washed with methanol, and then dried in a hot air dryer at 50° C. for 24 hours. The obtained crude product was dissolved in toluene, and column purification was performed using toluene as a developing solvent. The solvent was distilled off under reduced pressure from the solution after purification, and the resultant was dried in a hot air dryer at 50° C. for 24 hours to obtain 0.11 parts of the compound represented by No. 12 in the above specific compound examples as a dark brown solid. The maximum absorption wavelength of this compound in toluene was 651 nm.

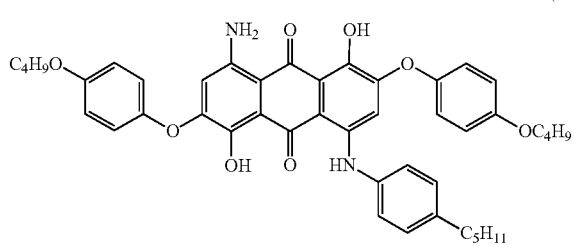

(18)

Example 9 (Synthesis of Anthraquinone Compound of Present Invention Represented by No. 15 in Specific Compound Examples)

To 20 parts of NMP, 0.9 parts of a compound represented by the following formula (19), 0.02 parts of copper powder, 0.02 parts of copper iodide, 2.0 parts of 4-iodobenzonitrile, 0.02 parts of potassium carbonate, and 0.15 parts of sodium acetate were added, the mixture was stirred at 140 to 150° C. for 12 hours, the reaction solution was then cooled to 25° C., 200 parts of methanol was added, and the mixture was further stirred for 1 hour. The reaction product was collected by filtration, washed with methanol, and then dried in a hot air dryer at 50° C. for 24 hours. The obtained crude product was dissolved in toluene, and column purification was performed using toluene as a developing solvent. The solvent was distilled off under reduced pressure from the solution after purification, and the resultant was dried in a hot air dryer at 50° C. for 24 hours to obtain 0.1 parts of the compound represented by No. 15 in the above specific compound examples as a dark brown solid. The maximum absorption wavelength of this compound in toluene was 651 nm.

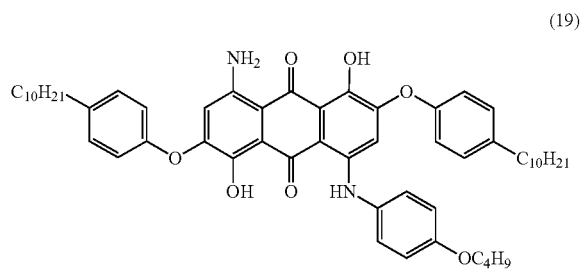

(19)

Example 10 (Synthesis of Anthraquinone Compound of Present Invention Represented by No. 18 in Specific Compound Examples)

To 20 parts of NMP, 0.9 parts of a compound represented by the following formula (20), 0.02 parts of copper powder, 0.02 parts of copper iodide, 4.0 parts of 2-ethylhexyl 4-iodobenzoate, 0.02 parts of potassium carbonate, and 0.15 parts of sodium acetate were added, the mixture was stirred at 140 to 150° C. for 12 hours, the reaction solution was then cooled to 25° C., 200 parts of methanol was added, and the mixture was further stirred for 1 hour. The reaction product was collected by filtration, washed with methanol, and then dried in a hot air dryer at 50° C. for 24 hours. The obtained crude product was dissolved in toluene, and column purification was performed using toluene as a developing solvent. The solvent was distilled off under reduced pressure from the solution after purification, and the resultant was dried in a hot air dryer at 50° C. for 24 hours to obtain 0.1 parts of the compound represented by No. 18 in the above specific compound examples as a dark brown solid. The maximum absorption wavelength of this compound in toluene was 651 nm.

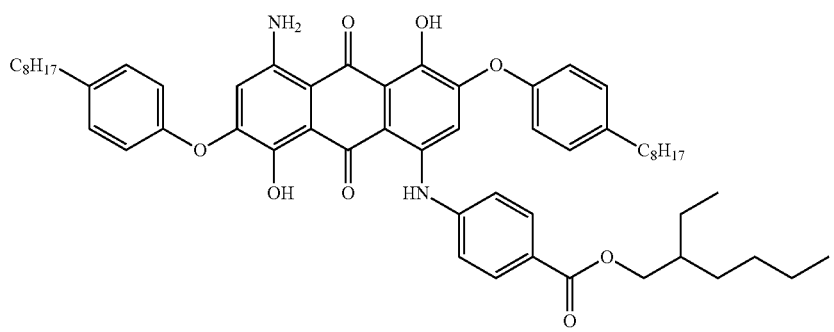

(20)

Example 11 (Synthesis of Anthraquinone Compound of Present Invention Represented by No. 24 in Specific Compound Examples)

To 20 parts of NMP, 0.9 parts of a compound represented by the following formula (21), 0.025 parts of copper powder, 0.025 parts of copper iodide, 2.0 parts of 2-iodobenzotrifluoride, 0.02 parts of potassium carbonate, and 0.15 parts of sodium acetate were added, the mixture was stirred at 150 to 160° C. for 12 hours, the reaction solution was then cooled to 25° C., 200 parts of methanol was added, and the mixture was further stirred for 1 hour. The reaction product was collected by filtration, washed with methanol, and then dried in a hot air dryer at 50° C. for 24 hours. The obtained crude product was dissolved in toluene, and column purification was performed using toluene as a developing solvent. The solvent was distilled off under reduced pressure from the solution after purification, and the resultant was dried in a hot air dryer at 50° C. for 24 hours to obtain 0.07 parts of the compound represented by No. 24 in the above specific compound examples as a dark brown solid. The maximum absorption wavelength of this compound in toluene was 649 nm.

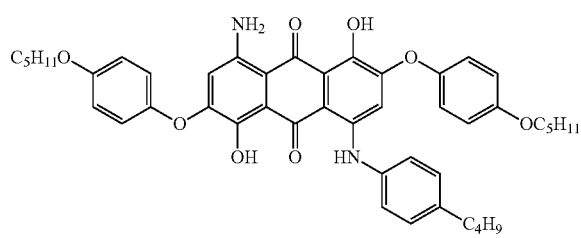

(21)

Example 12 (Synthesis of Anthraquinone Compound of Present Invention Represented by No. 28 in Specific Compound Examples)

To 20 parts of NMP, 0.9 parts of a compound represented by the following formula (22), 0.02 parts of copper powder, 0.02 parts of copper iodide, 2.0 parts of 3-iodobenzonitrile, 0.02 parts of potassium carbonate, and 0.15 parts of sodium acetate were added, the mixture was stirred at 140 to 150° C. for 12 hours, the reaction solution was then cooled to 25° C., 200 parts of methanol was added, and the mixture was further stirred for 1 hour. The reaction product was collected by filtration, washed with methanol, and then dried in a hot air dryer at 50° C. for 24 hours. The obtained crude product was dissolved in toluene, and column purification was performed using toluene as a developing solvent. The solvent was distilled off under reduced pressure from the solution after purification, and the resultant was dried in a hot air dryer at 50° C. for 24 hours to obtain 0.13 parts of the compound represented by No. 28 in the above specific compound examples as a dark brown solid. The maximum absorption wavelength of this compound in toluene was 650 nm.

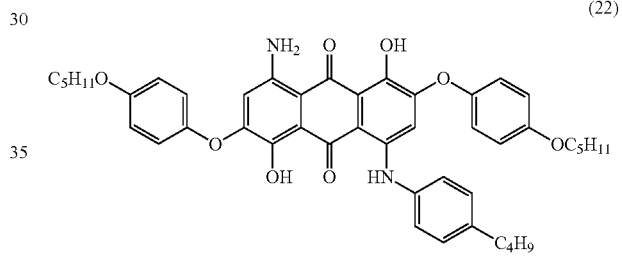

(22)

Example 13 (Synthesis of Anthraquinone Compound of Present Invention Represented by No. 33 in Specific Compound Examples)

To 20 parts of NMP, 0.9 parts of a compound represented by the following formula (23), 0.02 parts of copper powder, 0.02 parts of copper iodide, 2.0 parts of 1-fluoro-4-iodobenzene, 0.02 parts of potassium carbonate, and 0.15 parts of sodium acetate were added, the mixture was stirred at 140 to 150° C. for 12 hours, the reaction solution was then cooled to 25° C., 200 parts of methanol was added, and the mixture was further stirred for 1 hour. The reaction product was collected by filtration, washed with methanol, and then dried in a hot air dryer at 50° C. for 24 hours. The obtained crude product was dissolved in toluene, and column purification was performed using toluene as a developing solvent. The solvent was distilled off under reduced pressure from the solution after purification, and the resultant was dried in a hot air dryer at 50° C. for 24 hours to obtain 0.1 parts of the compound represented by No. 33 in the above specific compound examples as a brown solid. The maximum absorption wavelength of this compound in toluene was 652 nm.

(23)

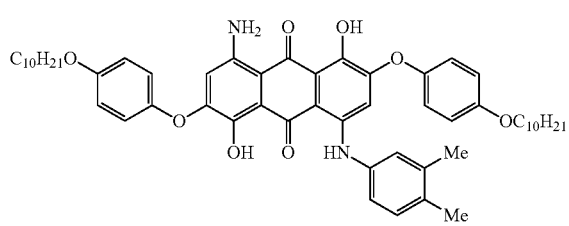

Example 14 (Synthesis of Anthraquinone Compound of Present Invention Represented by No. 35 in Specific Compound Examples)

To 20 parts of NMP, 0.9 parts of a compound represented by the following formula (24), 0.025 parts of copper powder, 0.025 parts of copper iodide, 2.5 parts of 3-fluoro-4-iodobenzonitrile, 0.02 parts of potassium carbonate, and 0.15 parts of sodium acetate were added, the mixture was stirred at 150 to 160° C. for 12 hours, the reaction solution was then cooled to 25° C., 200 parts of methanol was added, and the mixture was further stirred for 1 hour. The reaction product was collected by filtration, washed with methanol, and then dried in a hot air dryer at 50° C. for 24 hours. The obtained crude product was dissolved in toluene, and column purification was performed using toluene as a developing solvent. The solvent was distilled off under reduced pressure from the solution after purification, and the resultant was dried in a hot air dryer at 50° C. for 24 hours to obtain 0.04 parts of the compound represented by No. 35 in the above specific compound examples as a dark brown solid. The maximum absorption wavelength of this compound in toluene was 648 nm.

(24)

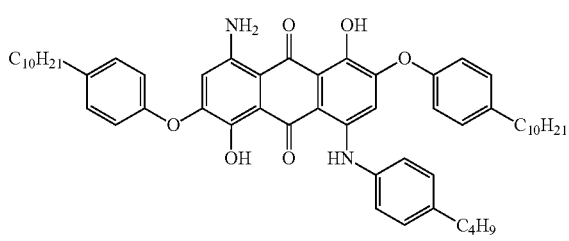

Example 15 (Synthesis of Anthraquinone Compound of Present Invention Represented by No. 37 in Specific Compound Examples)

To 20 parts of NMP, 0.9 parts of a compound represented by the following formula (25), 0.02 parts of copper powder, 0.02 parts of copper iodide, 2.0 parts of 1,2-difluoro-4-iodobenzene, 0.02 parts of potassium carbonate, and 0.15 parts of sodium acetate were added, the mixture was stirred at 140 to 150° C. for 12 hours, the reaction solution was then cooled to 25° C., 200 parts of methanol was added, and the mixture was further stirred for 1 hour. The reaction product was collected by filtration, washed with methanol, and then dried in a hot air dryer at 50° C. for 24 hours. The obtained crude product was dissolved in toluene, and column purification was performed using toluene as a developing solvent. The solvent was distilled off under reduced pressure from the solution after purification, and the resultant was dried in a hot air dryer at 50° C. for 24 hours to obtain 0.07 parts of the compound represented by No. 37 in the above specific compound examples as a dark brown solid. The maximum absorption wavelength of this compound in toluene was 650 nm.

(25)

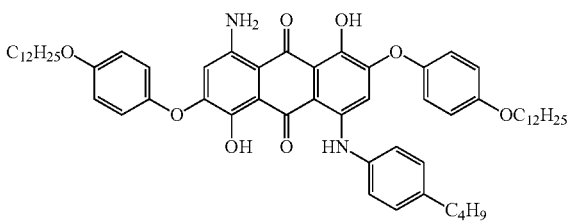

Example 16 (Synthesis of Anthraquinone Compound of Present Invention Represented by No. 46 in Specific Compound Examples)

To 20 parts of NMP, 0.9 parts of a compound represented by the following formula (26), 0.03 parts of copper powder, 0.03 parts of copper iodide, 2.0 parts of 4-bromo-2-fluoroanisole, 0.02 parts of potassium carbonate, and 0.15 parts of sodium acetate were added, the mixture was stirred at 150 to 160° C. for 12 hours, the reaction solution was then cooled to 25° C., 200 parts of methanol was added, and the mixture was further stirred for 1 hour. The reaction product was collected by filtration, washed with methanol, and then dried in a hot air dryer at 50° C. for 24 hours. The obtained crude product was dissolved in toluene, and column purification was performed using toluene as a developing solvent. The solvent was distilled off under reduced pressure from the solution after purification, and the resultant was dried in a hot air dryer at 50° C. for 24 hours to obtain 0.03 parts of the compound represented by No. 46 in the above specific compound examples as a dark brown solid. The maximum absorption wavelength of this compound in toluene was 654 nm.

(26)

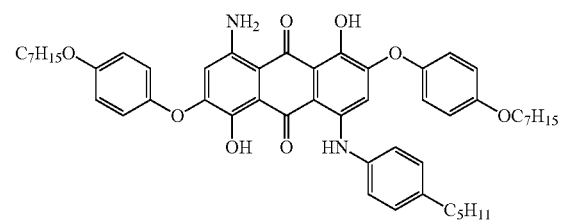

Example 17 (Synthesis of Anthraquinone Compound of Present Invention Represented by No. 51 in Specific Compound Examples)

To 20 parts of NMP, 0.9 parts of a compound represented by the following formula (27), 0.03 parts of copper powder, 0.03 parts of copper iodide, 2.5 parts of 1-bromo-3,4,5-trifluorobenzene, 0.02 parts of potassium carbonate, and 0.15 parts of sodium acetate were added, the mixture was stirred at 150 to 160° C. for 12 hours, the reaction solution was then cooled to 25° C., 200 parts of methanol was added, and the mixture was further stirred for 1 hour. The reaction product was collected by filtration, washed with methanol, and then dried in a hot air dryer at 50° C. for 24 hours. The obtained crude product was dissolved in toluene, and column purification was performed using toluene as a developing solvent. The solvent was distilled off under reduced pressure from the solution after purification, and the resultant was dried in a hot air dryer at 50° C. for 24 hours to obtain 0.06 parts of the compound represented by No. 51 in the above specific compound examples as a dark brown solid. The maximum absorption wavelength of this compound in toluene was 649 nm.

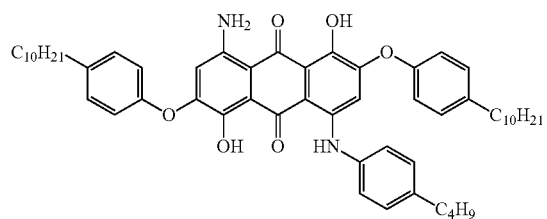

(27)

Synthesis Example 1 (Synthesis of Compound for Comparison)

A compound represented by the following formula (X) was obtained in accordance with the description of Example 6 in JPS62-5941A.

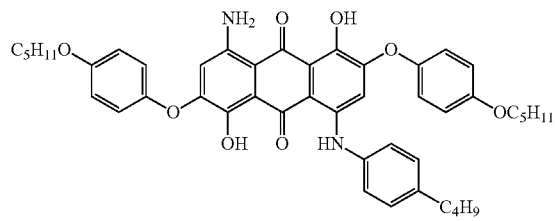

(X)

Example 18 (Preparation of Liquid Crystal Composition of Present Invention)

A liquid crystal composition of the present invention was obtained by mixing 0.006 parts of the compound represented by No. 8 in the specific compound examples obtained in Example 1, 0.306 parts of 1-cyano-4'-n-pentylbiphenyl, 0.15 parts of 1-cyano-4'-n-heptylbiphenyl, 0.096 parts of 1-cyano-4'-n-octyloxybiphenyl, and 0.048 parts of 1-cyano-4"-n-pentylterphenyl at room temperature.

Examples 19 to 34 and Comparative Example 1 (Preparation of Liquid Crystal Compositions of Present Invention and Liquid Crystal Composition for Comparison)

Liquid crystal compositions of the present invention and a liquid crystal composition for comparison were each obtained in accordance with Example 1, except that the compound represented by No. 8 obtained in Example 1 was replaced with the compound represented by No. 9 in specific compound examples obtained in Example 2, the compound represented by No. 10 in specific compound examples obtained in Example 3, the compound represented by No. 19 in specific compound examples obtained in Example 4, the compound represented by No. 5 in specific compound examples obtained in Example 5, the compound represented by No. 7 in specific compound examples obtained in Example 6, the compound represented by No. 11 in specific compound examples obtained in Example 7, the compound represented by No. 12 in specific compound examples obtained in Example 8, the compound represented by No. 15 in specific compound examples obtained in Example 9, the compound represented by No. 18 in specific compound examples obtained in Example 10, the compound represented by No. 24 in specific compound examples obtained in Example 11, the compound represented by No. 28 in specific compound examples obtained in Example 12, the compound represented by No. 33 in specific compound examples obtained in Example 13, the compound represented by No. 35 in specific compound examples obtained in Example 14, the compound represented by No. 37 in specific compound examples obtained in Example 15, the compound represented by No. 46 in specific compound examples obtained in Example 16, the compound represented by No. 51 in specific compound examples obtained in Example 17, or the compound for comparison represented by formula (X) obtained in Synthesis Example 1, respectively.

Example 35 (Production of Light control Element of Present Invention)

The liquid crystal composition obtained in Example 18 was encapsulated in an element made of two upper and lower glass substrates each having a transparent electrode with an inter-substrate gap of 15 μm, in which the surface of each glass substrate in contact with a liquid crystal was rubbed with a polyamide-based resin and was subjected to a homogeneous orientation treatment. In the element thus obtained, the liquid crystal was in a homogeneously oriented state when no voltage was applied, and dye molecules (the anthraquinone compound obtained in Example 1) were also in the same orientation according to the liquid crystal.

Examples 36 to 51 and Comparative Example 2 (Production of Light control Elements of Present Invention and Light control Element for Comparison)

Light control elements of the present invention and a light control element for comparison were each produced in accordance with Example 35, except that the liquid crystal composition obtained in Example 18 was replaced with each of the liquid crystal compositions obtained in Examples 19 to 34 and Comparative Example 1.
(Light Resistance Test of Light Control Element)
A UV cut filter of 380 nm or less was attached to the light control element obtained in each of Examples 35 to 51 and Comparative Example 2, and the light control element was irradiated with light for 100 hours with a metal halide lamp having an illuminance of 650 W/m$^2$ under the condition of 63° C. to be subjected to a light resistance test. For the light control elements before and after the light resistance test, the transmittances in a range of 380 to 780 nm in the case of applying no voltage and in the case of applying a voltage (100 V) were each measured with a spectrophotometer. The chromaticity (L*, a*, b*) was calculated from the obtained transmission spectrum in accordance with JIS Z 8781-4: 2013, and the color differences (ΔEab) before and after the light resistance test in the case of applying no voltage and in the case of applying a voltage (100V) were each calculated by the following calculation formula. This means that the smaller the value of ΔEab is, the smaller the color change before and after the light resistance test is and the better the light resistance is. The results are shown in Table 1.

$$\Delta Eab(L^*, a^*, b^*) = \{(\Delta L^*)^2 + (\Delta a^*)^2 + (\Delta b^*)^2\}^{1/2}$$

TABLE 1

Evaluation results of light resistance of light control element

| Light control element (Anthraquinone compound) | ΔEab | |
|---|---|---|
| | At time of applying no voltage | At time of applying voltage (100 V) |
| Example 35 (Specific example No. 8) | 5.2 | 4.0 |
| Example 36 (Specific example No. 9) | 4.0 | 3.2 |
| Example 37 (Specific example No. 10) | 3.5 | 2.3 |
| Example 38 (Specific example No. 19) | 5.7 | 4.7 |
| Example 39 (Specific example No. 5) | 6.0 | 4.2 |
| Example 40 (Specific example No. 7) | 7.5 | 6.2 |
| Example 41 (Specific example No. 11) | 5.2 | 4.5 |
| Example 42 (Specific example No. 12) | 5.5 | 4.3 |
| Example 43 (Specific example No. 15) | 6.5 | 5.5 |
| Example 44 (Specific example No. 18) | 5.9 | 4.4 |
| Example 45 (Specific example No. 24) | 7.1 | 6.1 |
| Example 46 (Specific example No. 28) | 6.2 | 5.1 |
| Example 47 (Specific example No. 33) | 8.5 | 7.0 |
| Example 48 (Specific example No. 35) | 9.1 | 7.5 |
| Example 49 (Specific example No. 37) | 8.2 | 6.9 |
| Example 50 (Specific example No. 46) | 9.2 | 7.7 |
| Example 51 (Specific example No. 51) | 9.5 | 8.0 |
| Comparative Example 2 (Formula (X)) | 15.0 | 10.0 |

As shown in Table 1, it was confirmed that the light control elements of Examples 35 to 51 each had a smaller color difference before and after the light resistance test than the light control element of Comparative Example 2 in both the case of applying no voltage and the case of applying a voltage (100 V), and had excellent light resistance.

Example 52 (Preparation of Liquid Crystal Composition of Present Invention and Production of Black Light control Element)

To the liquid crystal composition obtained in Example 19, 0.005 parts of a compound represented by the following formula (30) and 0.006 parts of a compound represented by the following formula (31) were further added and the mixture was mixed at room temperature to obtain a black liquid crystal composition of the present invention.

A black light control element was produced in accordance with Example 35, except that the liquid crystal composition obtained in Example 18 was substituted by the black liquid crystal composition obtained above. The average transmittance difference at 400 to 700 nm of the obtained black light control element was 31%, indicating high contrast.

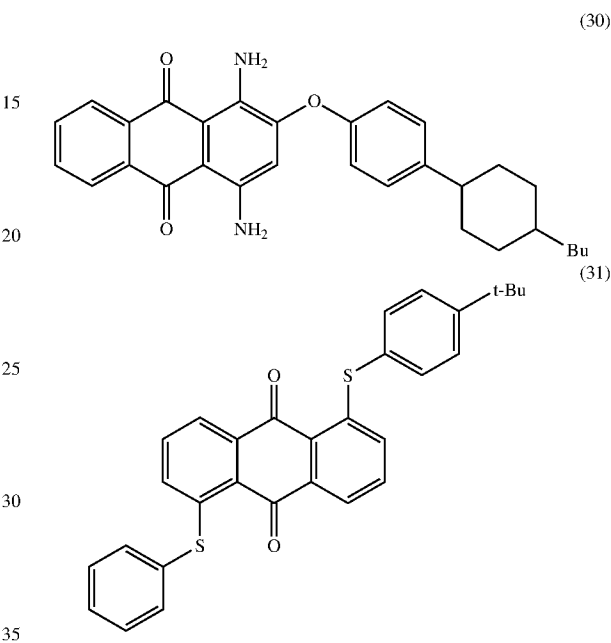

Example 53 (Preparation of Liquid Crystal Composition of Present Invention and Production of Black Light control Element)

A liquid crystal composition of the present invention was obtained by stirring 0.467 parts of isobornyl acrylate (manufactured by OSAKA ORGANIC CHEMICAL INDUSTRY LTD.) as a monofunctional monomer of a photocurable compound, 0.024 parts of triethylene glycol dimethacrylate (manufactured by SHIN-NAKAMURA CHEMICAL CO, LTD.) as a bifunctional monomer of a photocurable compound, 0.255 parts of 1-cyano-4'-n-pentylbiphenyl, 0.125 parts of 1-cyano-4'-n-heptylbiphenyl, 0.080 parts of 1-cyano-4'-n-octyloxybiphenyl, and 0.040 parts of 1-cyano-4"-n-pentylterphenyl as liquid crystal materials, 0.005 parts of IRGACURE TPO (manufactured by BASF) and 0.005 parts of IRGACURE 184 (manufactured by BASF) as photopolymerization initiators, and 0.01 parts of the compound represented by No. 9 in specific compound examples obtained in Example 2, and additionally 0.009 parts of the compound represented by the above formula (30) and 0.007 parts of the compound represented by the above formula (31) at room temperature for 2 hours, then adding 0.010 parts of a spacer agent ("Micropearl (registered trademark) SP220" manufactured by SEKISUI CHEMICAL CO., LTD.) having a diameter of 20 µm, and further mixing the mixture at room temperature.

The liquid crystal composition containing the spacer agent was applied onto an ITO film of a 5-cm square PET film provided with the ITO film by an applicator to form a liquid crystal composition layer. Next, this film and another 5-cm square PET film, which was the same as described above and was provided with an ITO film, were superimposed so that the liquid crystal composition layer provided on the ITO film faced the other ITO film. Thereafter, the thus obtained laminate of the two films and the liquid crystal composition layer was set at a position where the intensity of light from an LED lamp at 365 nm was 9 mW/cm² while being maintained at 23° C. with a thermoplate, and light irradiation was performed for 1 minute to photocure the photocurable compound, thereby producing a black light control element. The average transmittance difference at 400 to 700 nm of the obtained black light control element was 29%, indicating high contrast.

(Light Resistance Test of Black Light Control Element)

The black light control element obtained in each of Examples 52 and 53 was subjected to a light resistance test by light irradiation for 500 hours with a xenon lamp having an illuminance of 60 W/m² under the condition of 63° C. For the light control elements before and after the light resistance test, the transmittances in a range of 380 to 780 nm in the case of applying no voltage and in the case of applying a voltage (100 V) were each measured with a spectrophotometer. The chromaticity (L*, a*, b*) was calculated from the obtained transmission spectrum in accordance with JIS Z 8781-4:2013, and the color differences (ΔEab) before and after the light resistance test in the case of applying no voltage and in the case of applying a voltage (100V) were each calculated by the following calculation formula. This means that the smaller the value of ΔEab is, the smaller the color change before and after the light resistance test is and the better the light resistance is.

$$\Delta Eab(L^*, a^*, b^*) = \{(\Delta L^*)^2 + (\Delta a^*)^2 + (\Delta b^*)^2\}^{1/2}$$

The black light control elements obtained in Examples 52 and 53 each had a color difference (ΔEab) of 3 or less at the time of applying no voltage and at the time of applying a voltage even after a lapse of 500 hours in the xenon light resistance test, and were also excellent in light resistance at the time of long-time exposure to light. This result showed that the black light control elements of Examples 52 and 53 were black liquid crystal light control elements having high light resistance.

By using the liquid crystal composition of the present invention, a liquid crystal element for light control having high light resistance can be obtained. Such a light control element can be suitably used for outdoor building material applications and in-vehicle applications requiring high durability.

INDUSTRIAL APPLICABILITY

Since the anthraquinone compound of the present invention has dichroism and is excellent in light resistance, by using a liquid crystal composition containing the compound, a liquid crystal element for light control having high contrast and high light resistance can be obtained. Such a light control element can be suitably used for outdoor building material applications and in-vehicle applications requiring high durability.

The invention claimed is:

1. An anthraquinone compound being a dichroic dye compound represented by the following formula (1):

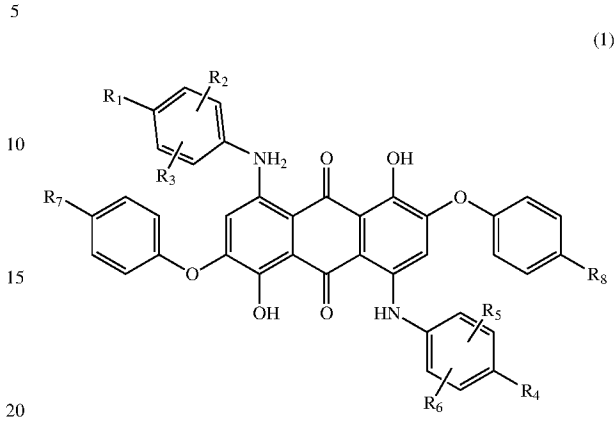

wherein $R_1$ and $R_4$ each independently represent a hydrogen atom, a C1-C12 linear alkyl group or a C3-C12 branched alkyl group, a C1-C12 linear alkoxy group or a C3-C12 branched alkoxy group, a halogen atom, —$CO_2R_9$, —$OCOR_9$, —$COR_9$, a cyano group, or a trifluoromethyl group, $R_2$, $R_3$, $R_5$, and $R_6$ each independently represent a hydrogen atom, a C1-C4 linear alkoxy group or a C3-C4 branched alkyl group, a C1-C4 linear alkoxy group or a C3-C4 branched alkoxy group, a halogen atom, —$CO_2R_9$, —$OCOR_9$, —$COR_9$, a cyano group, or a trifluoromethyl group, $R_7$ and $R_8$ each independently represent a hydrogen atom, a C1-C12 linear alky group or a C3-C12 branched alkyl group, or a C1-C12 linear alkoxy group or a C3-C12 branched alkoxy group, and $R_9$ each independently represents a C1-C12 linear alkyl group or a C3-C12 branched alkyl group or a substituent represented by the following formula (a):

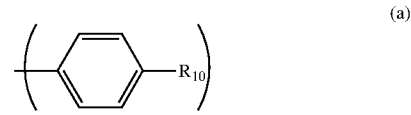

(wherein $R_{10}$ represents a hydrogen atom, a C1-C8 linear or alkyl group or a C3-C8 branched alkyl group or a C1-C8 linear alkoxy group or C3-C8 branched alkoxy group) or represented by the following formula (b):

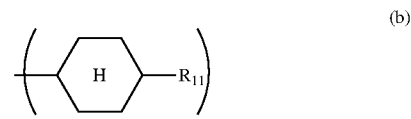

(wherein $R_{11}$ represents a hydrogen atom or a C1-C8 linear alkyl group or a C3-C8 branched alkyl group), provided that at least one of $R_1$ to $R_6$ represents a halogen atom, —$CO_2R_9$, —$COR_9$, a cyano group, or a trifluoromethyl group.

2. The anthraquinone compound according to claim 1, wherein $R_9$ is each independently a C1-C8 linear alkyl group or a C3-C8 branched alkyl group.

3. The anthraquinone compound according to claim 2, wherein in formula (1), $R_1$ and $R_4$ are each independently a hydrogen atom, a C1-C12 linear alkyl group or a C3-C12 branched alkyl group, a C1-C12 linear alkoxy group or a C3-C12 branched alkoxy group, a fluorine atom, a chlorine atom, —$CO_2R_9$, —$COR_9$, a cyano group, or a trifluoromethyl group, and $R_2$, $R_3$, $R_5$, and $R_6$ are each independently a hydrogen atom, a C1-C4 linear alkyl group or a C3-C4 branched alkyl group, a C1-C4 linear alkoxy group or a C3-C4 branched alkoxy group, a fluorine atom, a chlorine atom, —$CO_2R_9$, —$COR_9$, a cyano group, or a trifluoromethyl group.

4. The anthraquinone compound according to claim 3, wherein in formula (1), $R_1$ and $R_4$ are each independently a hydrogen atom, a C1-C12 linear alkyl group or a C3-C12 branched alkyl group, a fluorine atom, —$CO_2R_9$, —$COR_9$, a cyano group, or a trifluoromethyl group, and $R_2$, $R_3$, $R_5$, and $R_6$ are each independently a hydrogen atom, a C1-C4 linear alkyl group or a C3-C4 branched alkyl group, a fluorine atom, —$CO_2R_9$, —$COR_9$, a cyano group, or a trifluoromethyl group.

5. The anthraquinone compound according to claim 3, wherein in formula (1), $R_2$ and $R_5$ are a hydrogen atom.

6. The anthraquinone compound according to claim 5, wherein in formula (1), only one of $R_1$ and $R_3$ is a hydrogen atom, and only one of $R_4$ and $R_6$ is a hydrogen atom.

7. The anthraquinone compound according to claim 5, wherein in formula (1), $R_3$ and $R_6$ are a hydrogen atom.

8. The anthraquinone compound according to claim 7, wherein in formula (1), $R_4$ is a C4-C12 linear or branched alkyl group.

9. The anthraquinone compound according to claim 1, wherein in formula (1), $R_7$ and $R_6$ are each independently a C4-C12 linear or branched alkyl group or a C4-C12 linear or branched alkoxy group.

10. A liquid crystal composition comprising the anthraquinone compound according to claim 1 and a liquid crystal material.

11. The liquid crystal composition according to claim 10, further comprising at least one or more dye compounds other than the anthraquinone compound represented by formula (1).

12. The liquid crystal composition according to claim 10, further comprising a photocurable compound and a photopolymerization initiator.

13. A photocured product of the liquid crystal composition according to claim 12.

14. A light control element comprising the liquid crystal composition according to claim 10 sandwiched between a pair of substrates disposed opposite to each other, at least one of which is a transparent substrate having a transparent electrode.

15. A light control element comprising the photocured product according to claim 13 sandwiched between a pair of substrates disposed opposite to each other, at least one of which is a transparent substrate having a transparent electrode.

* * * * *